United States Patent
Rowe

(10) Patent No.: US 11,459,883 B2
(45) Date of Patent: Oct. 4, 2022

(54) PLASMA CHEMISTRY DERIVED FORMATION ROCK EVALUATION FOR PULSE POWER DRILLING

(71) Applicant: Halliburton Energy Services, Inc., Houston, TX (US)

(72) Inventor: Mathew Dennis Rowe, Spring, TX (US)

(73) Assignee: Halliburton Energy Services, Inc., Houston, TX (US)

( * ) Notice: Subject to any disclaimer, the term of this patent is extended or adjusted under 35 U.S.C. 154(b) by 87 days.

(21) Appl. No.: 17/006,254

(22) Filed: Aug. 28, 2020

(65) Prior Publication Data

US 2022/0065103 A1    Mar. 3, 2022

(51) Int. Cl.
*E21B 49/00* (2006.01)
*E21B 7/15* (2006.01)
*G01N 33/28* (2006.01)

(52) U.S. Cl.
CPC ............. *E21B 49/005* (2013.01); *E21B 7/15* (2013.01); *G01N 33/2823* (2013.01)

(58) Field of Classification Search
CPC ...... E21B 49/005; E21B 7/15; G01N 33/2823
See application file for complete search history.

(56) References Cited

U.S. PATENT DOCUMENTS

| | | | |
|---|---|---|---|
| 1,720,325 A * | 7/1929 | Hackstaff | G01V 3/20 436/28 |
| 2,328,555 A | 9/1943 | Hoover, Jr. | |
| 2,700,897 A | 2/1955 | Arps | |
| 4,536,713 A | 8/1985 | Davis et al. | |
| 4,741,405 A | 5/1988 | Moeny et al. | |
| 4,980,642 A | 12/1990 | Rodney | |
| 5,005,406 A | 4/1991 | Jasinski et al. | |
| 5,140,527 A | 8/1992 | Jones et al. | |
| 5,163,029 A | 11/1992 | Bryant et al. | |
| 5,896,938 A | 4/1999 | Moeny et al. | |

(Continued)

FOREIGN PATENT DOCUMENTS

| | | |
|---|---|---|
| CN | 102678044 A | 9/2012 |
| CN | 202596572 U | 12/2012 |

(Continued)

OTHER PUBLICATIONS

"Isotope Logging: Continuous isotopic ratio measurement service", [online] retrieved on Jun. 1, 2020 from https://www.slb.com/-/media/files/geoservices/product-sheet/isotope-logging-ps.ashx, 2015, 2 pages.

(Continued)

*Primary Examiner* — D. Andrews
(74) *Attorney, Agent, or Firm* — Delizio, Peacock, Lewin & Guerra

(57) ABSTRACT

During pulse power drilling, the formation rock type is determined by analyzing organic and inorganic chemical reaction products. Plasma pulses interact with the solid rock of the formation to shift downhole chemical reactions. The formation type may act as a catalyst or an inhibitor to enhance or degrade reactions. The concentration of organic and inorganic chemical reaction products is determined by analyzing the reactions occurring at the drill bit. From the concentrations, the formation rock type is determined.

20 Claims, 10 Drawing Sheets

(56) References Cited

U.S. PATENT DOCUMENTS

| | | |
|---|---|---|
| 6,026,099 A | 2/2000 | Young |
| 6,104,022 A | 8/2000 | Young et al. |
| 6,176,323 B1 | 1/2001 | Weirich et al. |
| 6,761,416 B2 | 7/2004 | Moeny |
| 7,124,030 B2 | 10/2006 | Ellis |
| 7,174,254 B2 | 2/2007 | Ellis |
| 7,337,660 B2 | 3/2008 | Ibrahim et al. |
| 7,384,009 B2 | 6/2008 | Moeny |
| 7,416,032 B2 | 8/2008 | Moeny et al. |
| 7,527,108 B2 | 5/2009 | Moeny |
| 7,529,626 B1 | 5/2009 | Ellis |
| 7,530,406 B2 | 5/2009 | Moeny et al. |
| 7,559,378 B2 | 7/2009 | Moeny |
| 7,571,644 B2 | 8/2009 | Ibrahim et al. |
| 7,959,094 B2 | 6/2011 | Moeny |
| 8,083,008 B2 | 12/2011 | Moeny |
| 8,172,006 B2 | 5/2012 | Moeny |
| 8,186,454 B2 | 5/2012 | Moeny |
| 8,567,522 B2 | 10/2013 | Moeny |
| 8,575,541 B1 | 11/2013 | Jamison et al. |
| 8,616,302 B2 | 12/2013 | Moeny |
| 8,789,772 B2 | 7/2014 | Moeny |
| 8,810,794 B2 | 8/2014 | Breviere et al. |
| 9,010,458 B2 | 4/2015 | Moeny |
| 9,016,359 B2 | 4/2015 | Moeny |
| 9,190,190 B1 | 11/2015 | Moeny |
| 9,335,438 B2 | 5/2016 | Jamison et al. |
| 9,700,893 B2 | 7/2017 | Moeny |
| 9,765,617 B2 | 9/2017 | Gosney et al. |
| 10,001,465 B2 | 6/2018 | Mitchell et al. |
| 10,113,364 B2 | 10/2018 | Moeny et al. |
| 10,371,691 B2 | 8/2019 | Strapoc et al. |
| 10,407,995 B2 | 9/2019 | Moeny |
| 10,641,757 B2 | 5/2020 | Rowe |
| 2005/0150688 A1* | 7/2005 | MacGregor ............ E21B 7/15 175/16 |
| 2006/0037516 A1 | 2/2006 | Moeny |
| 2007/0137893 A1 | 6/2007 | Moeny et al. |
| 2007/0152494 A1 | 7/2007 | Moeny |
| 2008/0147326 A1 | 6/2008 | Ellis |
| 2008/0277508 A1 | 11/2008 | Moeny |
| 2009/0126928 A1 | 5/2009 | Sumrall et al. |
| 2010/0250142 A1 | 9/2010 | Zamora et al. |
| 2011/0000713 A1 | 1/2011 | Meeten et al. |
| 2011/0251795 A1 | 10/2011 | Difoggio |
| 2012/0298421 A1 | 11/2012 | Coates et al. |
| 2013/0032404 A1 | 2/2013 | Donderici et al. |
| 2014/0008968 A1 | 1/2014 | Moeny |
| 2015/0068806 A1 | 3/2015 | Duran Toro et al. |
| 2015/0260035 A1 | 9/2015 | Rowe et al. |
| 2015/0308235 A1 | 10/2015 | Moeny |
| 2015/0322326 A1 | 11/2015 | Van Slyke et al. |
| 2015/0354352 A1 | 12/2015 | Ezzat et al. |
| 2016/0010450 A1 | 1/2016 | Donderici et al. |
| 2016/0115786 A1 | 4/2016 | Breviere et al. |
| 2017/0175505 A1 | 6/2017 | Curlett |
| 2017/0226851 A1 | 8/2017 | Hakami et al. |
| 2018/0148981 A1 | 5/2018 | Moeny |
| 2019/0003298 A1 | 1/2019 | Stolyarov et al. |
| 2019/0226336 A1 | 7/2019 | Benson et al. |
| 2019/0368345 A1* | 12/2019 | Rowe ............... G01N 33/2823 |
| 2019/0376386 A1 | 12/2019 | Wright et al. |
| 2020/0217143 A1 | 7/2020 | Liu et al. |
| 2020/0224498 A1 | 7/2020 | Liu et al. |
| 2022/0065044 A1 | 3/2022 | Rowe |
| 2022/0065102 A1 | 3/2022 | Rowe |
| 2022/0065105 A1 | 3/2022 | Rowe |
| 2022/0065107 A1 | 3/2022 | Rowe |
| 2022/0065769 A1 | 3/2022 | Rowe |

FOREIGN PATENT DOCUMENTS

| | | |
|---|---|---|
| EP | 0700068 A1 | 3/1996 |
| EP | 1508794 A1 | 2/2005 |
| RU | 2477370 C1 | 3/2013 |
| WO | 9806234 A1 | 2/1998 |
| WO | 9937581 A2 | 7/1999 |
| WO | 2006023998 A2 | 3/2006 |
| WO | 2008097101 A1 | 8/2008 |
| WO | 2013110328 A1 | 8/2013 |
| WO | 2014100255 A1 | 6/2014 |
| WO | 2015124733 A2 | 8/2015 |
| WO | 2015154876 A1 | 10/2015 |
| WO | 2017030614 A1 | 2/2017 |
| WO | 2017146673 A1 | 8/2017 |
| WO | 2018071020 A1 | 4/2018 |
| WO | 2018136033 A1 | 7/2018 |
| WO | 2018186828 A1 | 10/2018 |
| WO | 2019245544 A1 | 12/2019 |
| WO | 2019245545 A1 | 12/2019 |

OTHER PUBLICATIONS

Behrends, et al., "Ultrasonic Relaxation and Fast Chemical Kinetics of Some Carbohydrate Aqueous Solutions", 1997 American Chemical Society, J. Am. Chem. Soc. vol. 119 No. 9, pp. 2182-2186.

Berner, et al., "Maturity Related Mixing Model for Methane, Ethane and Propane, based on Carbon Isotopes", Advances in Organic Geochemistry, vol. 13, No. 1-3, 1988, 6 pages.

Bruggeman, et al., "Non-Thermal Plasmas in and in Contact With Liquids", Journal of Physics D: Applied Physics 42, 2009, 28 pages.

Canonica, et al., "Quantitative Structure—Activity Relationships for Oxidation Reactions of Organic Chemicals in Water", Environmental Toxicology and Chemistry, vol. 22 No. 8, 2003, pp. 1743-1754.

Carrasquillo, et al., "Radical Reactivity in the Condensed Phase: Intermolecular Versus Intramolecular Reactions of Alkoxy Radicals", 2015 American Chemical Society, J. Phys. Chem. Lett. 6, pp. 2388-2392.

Chernyak, et al., "Plasma Catalysis of Chemical Reactions", Problems of Atomic Science and Technology, Series: Plasma Physics, 2014, pp. 124-129.

Cruse, et al., "Geochemistry of Low-Molecular Weight Hydrocarbons in Hydrothermal Fluids from Middle Valley, northern Juan de Fuca Ridge", Geochimica et Cosmochimica Acta, vol. 70, Issue 8, Apr. 15, 2006, 54 pages, https://doi.org/10.1016/j.gca.2006.01.015, 2006.

Donahue, et al., "New Rate Constants for Ten Oh Alkane Reactions From 300 to 400 K: An Assessment of Accuracy", 1998 American Chemical Society, J. Phys. Chem. vol. 102 No. 18, pp. 3121-3126.

Gierczak, et al., "Rate Coefficients for the Reactions of Hydroxyl Radicals With Methane and Deuterated Methanes", 1997 American Chemical Society, J. Phys. Chem. A vol. 101 No. 17, pp. 3126-3134.

Goddard, et al., "Novel Gas Isotope Interpretation Tools to Optimize Gas Shale Production", Report to Research Partnership to Secure Energy for America, 2013, 90 pages.

Hidenori, et al., "Streamer Discharges in Liquids and Their Applications", Institute of Electrical and Electronics Engineers Transactions on Dielectrics and Electrical Insulation vol. 7 No. 5, Oct. 2000, pp. 646-653.

Jiang, et al., "Review on Electrical Discharge Plasma Technology for Wastewater Remediation", Chemical Engineering Journal 236, 2014, pp. 348-368.

Kirkpatrick, et al., "Hydrogen, Oxygen, and Hydrogen Peroxide Formation in Aqueous Phase Pulsed Corona Electrical Discharge", 2005 American Chemical Society, Ind. Eng. Chem. Res. vol. 44 No. 12, pp. 4243-4248.

Kwok, et al., "Alkoxy Radial Isomerization in the OH Radical-Initiated Reactions of C4-C8 N-Alkanes", 1996 American Chemical Society, J. Phys. Chem. vol. 100 No 1, pp. 214-219.

Laroussi, "Low-Temperature Plasmas for Medicine?", Institute of Electrical and Electronics Engineers Transactions on Plasma Science vol. 37 No. 6, Jun. 2009, pp. 714-725.

Locke, et al., "Analysis and Review of Chemical Reactions and Transport Processes in Pulsed Electrical Discharge Plasma Formed Directly in Liquid Water", Plasma Chem Plasma Process, 2012, pp. 875-917.

(56) References Cited

OTHER PUBLICATIONS

Locke, et al., "Review of the Methods to Form Hydrogen Peroxide in Electrical Discharge Plasma With Liquid Water", Plasma Sources Science and Technology 20, 2011, pp. 1-15.
Malik, et al., "Water Purification by Electrical Discharges", Institute of Physics Publishing, Plasma Sources Science and Technology 10, 2001, pp. 82-91.
Medodovic, et al., "Primary Chemical Reactions in Pulsed Electrical Discharge Channels in Water", Journal of Physics D: Applied Physics 40, 2007, pp. 7734-7736.
Minakata, et al., "Development of a Group Contribution Method to Predict Aqueous Phase Hydroxl Radical (HO) Reaction Rate Constants", 2009 American Chemical Society, Environ. Sci. Technol. vol. 43 No. 16, pp. 6220-6227.
Minakata, et al., "Linear Free Energy Relationships Between Aqueous Phase Hydroxyl Radical Reaction Rate Constants and Free Energy of Activation", 2011 American Chemical Society, Environmental Science & Technology 45, pp. 3479-3486.
Nair, et al., "Mud Gas Isotope Logging using Mass Spectrometry", Society of Petroleum Engineers,2009 SPE Asia Pacific Oil and Gas Conference and Exhibition, Aug. 4-6, 2009, Jakarta, Indonesia, 13 pages.
Pironti, et al., "Determination of the 13C/12C Carbon Isotope Ratio in Carbonates and Bicarbonates by 13C NMR Spectroscopy", American Chemical Society, Analytical Chemistry 2017, 89, 21, 11413-11418, Sep. 13, 2017.
Pourzamani, et al., "Natural Organic Matter Degradation Using Combined Process of Ultrasonic and Hydrogen Peroxide Treatment", Geosciences Institute Yearbook UFRJ, vol. 38 No. 1, 2015, pp. 63-72.
Rao, et al., "Geochemical Assessment of Light Gaseous Hydrocarbons in Near-Surface soils of Kutch-Saurashtra: Implication for Hydrocarbons Prospects", Indian Academy of Sciences, J. Earth Syst. Sci. 122, No. 1, 2013, 9 pages.
Sahni, et al., "Quantification of Hydroxyl Radicals Produced in Aqueous Phase Pulsed Electrical Discharge Reactors", 2006 American Chemical Society, Ind. Eng. Chem. Res. vol. 45 No. 17, 2006, pp. 5819-5825.
Schoell, "Genetic Characterization of Natural Gases", The American Association of Petroleum Geologists Bulletin, V. 67, No. 12, 1983, 14 pages.
Shih, et al., "Chemical and Physical Characteristics of Pulsed Electrical Discharge Within Gas Bubbles in Aqueous Solutions", Plasma Chem Plasma Process, 2009, pp. 1-20.
Storey, et al., "Water Vapour, Sonoluminescence and Sonochemistry", Royal Society Publishing, Proc R. Soc. Lond. A, 2000, pp. 1685-1709.
Sugiarto, et al., "Pulsed Plasma Processing of Organic Compounds in Aqueous Solution", Thin Solid Films 386, 2001, pp. 295-299.
Sugiarto, et al., "Transient Regime of Pulsed Breakdown in Low-Conductive Water Solutions", Institute of Physics Publishing, Journal of Physics D: Applied Physics 34, 2001, pp. 3400-3406.
Suslick, et al., "Alkane Sonochemistry", 1983 American Chemical Society, J. Phys. Chem. vol. 87 No. 13, pp. 2299-2301.
Thagard, et al., "Plasma Chemistry in Pulsed Electrical Discharge in Liquid", Transaction of the Materials Research Society of Japan, 2009, pp. 257-262.
Zare, et al., "High-precision optical measurements of 13C/12C isotope ratios in organic compounds at natural abundance", Proceedings of the National Academy of Science of the United States of America, PNAS Jul. 7, 2009 106(27) 10928-10932; ttps://doi.org/10.1073/pnas.0904230106.
PCT Application No. PCT/US2021/028780, International Search Report, dated Aug. 4, 2021, 3 pages.
PCT Application No. PCT/US2021/028780, Written Opinion, dated Aug. 4, 2021, 3 pages.
PCT Application No. PCT/US2021/031572, International Search Report, dated Aug. 23, 2021, 5 pages.
PCT Application No. PCT/US2021/031572, Written Opinion, dated Aug. 23, 2021, 5 pages.
PCT Application No. PCT/US2021/070776, International Search Report, dated Oct. 19, 2021, 5 pages.
PCT Application No. PCT/US2021/070776, Written Opinion, dated Oct. 19, 2021, 3 pages.
PCT Application No. PCT/US2021/070777, International Search Report, dated Oct. 18, 2021, 4 pages.
PCT Application No. PCT/US2021/070777, Written Opinion, dated Oct. 18, 2021, 6 pages.
PCT Application No. PCT/US2021/070815, International Search Report, dated Oct. 20, 2021, 3 pages.
PCT Application No. PCT/US2021/070815, Written Opinion, dated Oct. 20, 2021, 4 pages.
Bazargan, et al., "Wellbore Instability During Plasma Torch Drilling in Geothermal Reservoirs", 49th U.S. Rock Mechanics/Geomechanics Symposium, San Francisco, California, Jun. 28-Jul. 1, 2015, pp. 1-4.
Li, et al., "Influenceson High-Voltage Electro Pulse Boring in Granite", Energies, Sep. 17, 2018, vol. 11, No. 9, pp. 1-17, ISSN 2461.
"U.S. Appl. No. 17/006,051, Non-Final Office Action", dated May 2, 2022, 10 pages.
"U.S. Appl. No. 17/006,247 Office Action", dated Mar. 17, 2022, 6 pages.
Suhr, "Organic Syntheses Under Plasma Conditions", Plasma Chemistry, International Symposium on Plasma Chemistry 1974, University of Tübingen, Germany, Department of Chemistry, 1974, pp. 395-414.

* cited by examiner

PLASMA CHEMISTRY DERIVED FORMATION ROCK EVALUATION FOR PULSE POWER DRILLING

TECHNICAL FIELD

The disclosure generally relates to pulse power drilling operations, and in particular, to plasma chemistry derived formation rock evaluation for pulse power drilling.

BACKGROUND

Mud logging during drilling of a wellbore can provide information about geological formations and fluid. Such information can be correlated to petrophysical properties and depths within the formation during wellbore drilling based on testing and measurement of drilling mud returned to the surface. Drilling mud (also referred to as mud) is the fluid that can be pumped down the drill string in order to lubricate the bottom hole assembly and drill string, to suppress fluid or gas ingress into the bore hole and maintain pore pressure, and also to remove cuttings from the well as it circulates to the surface.

When wellbores are drilled in a geological formation, information about the formation layers and fluids—such as lithology, porosity, permeability, petrochemical type, petrochemical concentration, etc.—can be determined based on the chemical composition of the mud, cuttings, and dissolved gasses returned to the surface. In traditional mud logging, a record of the characteristics determined from the drilling mud can be kept as a function of drilling depth in order to correlate rock, fluid, and gas characteristics to layers and reservoirs at depths in the formation.

BRIEF DESCRIPTION OF THE DRAWINGS

Aspects of the disclosure may be better understood by referencing the accompanying drawings.

DESCRIPTION

Figure 1:
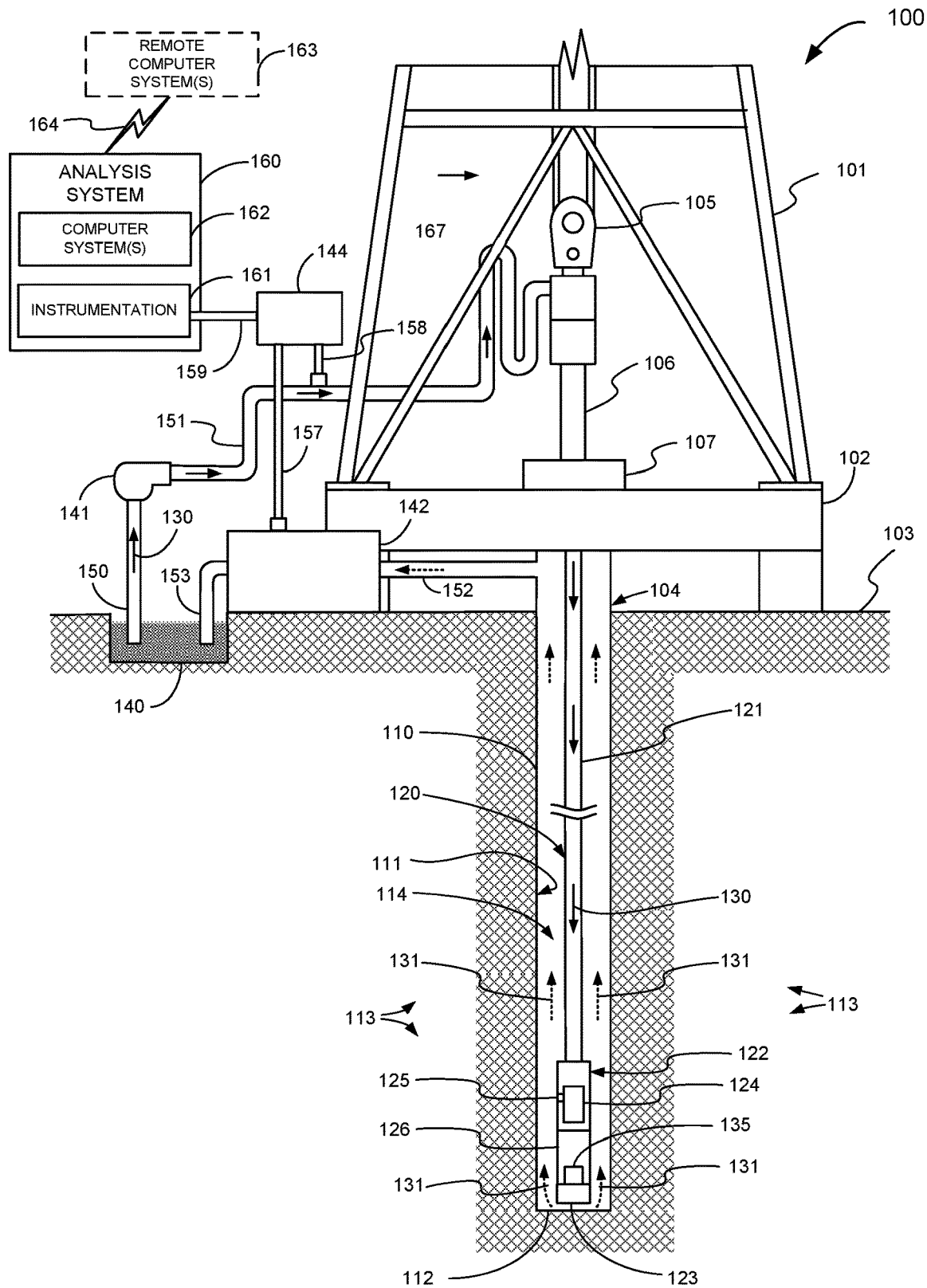
FIG. 1 depicts an example pulse power drilling system for mud logging, according to one or more embodiments.

The description that follows includes example systems, methods, techniques, and program flows that embody aspects of the disclosure. However, it is understood that this disclosure may be practiced without these specific details. For instance, this disclosure refers to pulsed direct current (DC) plasma in illustrative examples. Aspects of this disclosure can be also applied to sustained or alternating current (AC) plasmas. Additionally, while analysis may be described in reference to being performed at the surface of the borehole, example embodiments can include at least a partial analysis downhole. For example, some or all of the analysis can be performed in a downhole tool of the drill string. In other instances, well-known instruction instances, protocols, structures, and techniques have not been shown in detail in order not to obfuscate the description.

Overview

Formation evaluation is the analysis of subsurface formation characteristics, such as lithology, porosity, permeability, and saturation. Conventional techniques for formation evaluation characterize the subsurface environment before or during drilling through mud logging, wireline logging, coring, drill stem testing, measurement while drilling (MWD), or logging while drilling (LWD). While there are several different downhole methods for characterizing a formation, data density is often lacking. Additionally, these methods tend to produce bulk measurements that are not representative of the entire subsurface formation. By analyzing events at the bit using pulse plasma drilling, the rock type of the formation being drilled can be more accurately determined.

In pulse plasma drilling, a pulse plasma drill bit drills a wellbore using electric pulses that include short duration, periodic, high-voltage pulses that are discharged through the formation. Such discharges can create high internal pressure to break or fracture the rock from the inside (breaking from tension). Such pulse plasma drilling can involve generating a plasma, a high energy fluid, in the drilling fluid or rock downhole which functions as a high-energy discharge. Plasma can be a highly conductive, ionized gas containing free electrons and positive ions (from which the electrons have been disassociated). In the high temperature and high-pressure environment downhole, the creation of a plasma involves injecting large amounts of energy into the subsurface formation. Ideally, the energy would be injected entirely into the subsurface formation as mechanical crushing force. However, a portion of the energy may also be absorbed by the drilling fluid and/or the formation. For example, a portion of the energy may be absorbed by the drilling fluid when the drill string is not in contact with a bottom of the borehole when the energy is discharged from the electrodes of the drill string due to borehole irregularities, or due to bottom hole assembly geometry. The conductivity of the formation is independent of the formational fluid in the pore spaces of the formation. The independent conductivity allows for energy losses due to absorption by the formation to be distinguished from other losses.

Some embodiments can perform evaluation of the rock of the subsurface formation at or near the drill bit based on analysis of the chemistry changes of the downhole fluid that has interacted with the pulses of plasma emitted as part of the pulse power drilling. For example, an attribute of the subsurface formation (such as type of rock) can be determined based on this plasma chemistry analysis. Thus, the changes in chemistry of the downhole fluid can be correlated to an attribute of the subsurface formation that is at or near the drill bit.

For example, in response to the energy being injected into the subsurface formation, ionic bonds within the rock of the formation can be broken and solid rock from the formation and/or formation fluid can be vaporized. The energy output from the electrodes of the drill string can also create chemical reactions between the species downhole. These chemical reactions can generate chemically complex molecules which should be accounted for in mud logging because these complex molecules are not constituents of either the formation fluid or the drilling mud. The loss of energy to the formation can change the energy available for chemical reactions independent of the fluids. The reduction in energy for plasma-based chemistry can shift possible chemical reactions. This can be quantified through analysis of the resultant products. The energy shift can come in two forms. Either the possible formational compounds that can catalyze the reaction will change, or the aqueous or organic liquid phase reactions will shift. The application of the formation conductivity at the bit with possible chemical reactions allows the formation type to be determined from the formational and non-formational fluids produced at the surface by correlating the concentration of organic and inorganic chemical species to plasma generation parameters. Organic chemical species are chemical species or chemical compounds that can contain carbon and hydrogen, specifically carbon bonded to hydrogen, such as hydrocarbons. Inorganic chemical species are chemical species or compounds that do not contain carbon bonded to hydrogen. Examples of inorganic chemical species include salts, metals, substances made from single elements, and any other compounds that do not contain carbon bonded to hydrogen.

Example System

FIG. 1 illustrates a schematic diagram of a pulse power drilling system (a system 100), according to one or more embodiments. The system 100 as illustrated in FIG. 1 includes a derrick 101 positioned on a platform 102 that is located above a surface 103 and covering a wellhead 104. The wellhead 104 includes a borehole 110 that extends from the surface 103 into one or more layers of a subterranean formation 113. The borehole 110 may include borehole walls 111 that extend substantially vertically from surface 103 and parallel to one another, forming, and at least partially enclosing, the space within the borehole that extends from surface 103 to a borehole bottom surface 112. Although shown as having substantially a vertical orientation in FIG. 1, embodiments of the borehole 110 are not limited to vertically orientated boreholes, and may include at least some portion(s) of the borehole that extend at an angle relative to vertical, including in some embodiments portions of the borehole that may extend horizontally in a direction parallel to the surface 103.

The system 100 includes a drill string 120 that may be positioned over and extending downward into the borehole 110. The drill string 120 may be supported at an upper portion by a hoist 105 suspended from derrick 101 that allows the drill string 120 to be controllable lowered into and raised to different depths within the borehole 110, and/or inserted into and completely withdrawn from the borehole 110. The drill string 120 may be coupled to a hoist 105 through a kelly 106 and may extend through a rotary table 107 positioned adjacent to and/or extending though an opening in a platform 102. The rotary table 107 may be configured to maintain the position of the drill string 120 relative to the platform 102 as the drill string 120 is extended through the opening in the platform 102 and into the borehole 110. The drill string 120 may comprise a plurality of sections of drill pipe 121 coupling a lower or distal end of the drill string 120 to a bottom hole assembly (BHA) 122. The BHA 122 includes a pulse power drilling (PPD) assembly 126 having electrodes of the drill bit 123 and a pulse-generating circuit 135.

Referring again to FIG. 1, a drilling fluid 130, such as drilling mud, may be initially sourced from a fluid pit 140, which may be referred to as a "mud pit." Although, depicted below the surface 103, the mud pit can be equipment located on the surface 103 as well. A pump 141 may be used to suction the drilling fluid 130 from the fluid pit 140 through a fluid conduit 150, and provide a pressurized flow or circulation of the drilling fluid 130 through a fluid conduit 151 to the upper portion of the drill string 120, as illustratively represented by the solid line arrows included within the fluid conduits 150 and 151. The drilling fluid 130 may then proceed through the sections of the drill pipe 121 that make up portions of the drill string 120, providing a fluid passageway for the drilling fluid 130 to flow from the upper portion of the drill string 120 to the BHA 122 positioned within the drill string 120.

The flow of the drilling fluid 130 is directed through the BHA 122 and expelled from one or more ports included in the electrodes of the drill bit 123. The drilling fluid 131, as illustratively represented in FIG. 1 by dashed-line arrows, that has been expelled from ports on, or through, the electrodes of the drill bit 123 helps to remove formation material that has been broken up by the electrical energy generated at the electrodes of the drill bit 123 in a direction away from the electrodes of the drill bit 123 and away from a borehole bottom surface 112.

In addition to carrying away broken up formation material, the flow of a drilling fluid 131 may also represent drilling fluid that has been exposed to or that has otherwise interacted with the electrical energy being applied by the electrodes of the drill bit 123 to the borehole bottom surface 112 and/or to the drilling fluid in the vicinity of the electrodes of the drill bit 123. The drilling fluid 131 is illustrated as broken-line arrows to represent drilling fluid that may have one or more chemical properties and/or one or more physical properties of the drilling fluid that have been altered due to the interaction of the drilling fluid 131 with the electric energy provided by the electrodes of the drill bit 123. The flow of the drilling fluid 131 continues to flow back upward toward the surface 103 through the annulus 114 of the borehole 110. The annulus 114 are formed by the space between the borehole walls 111 and the outer surfaces of the drill string 120. The drilling fluid 130 flowing into the drill string 120 from the mud pit can be referred to as "influent," and the drilling fluid 131 flowing from the electrodes of the drill bit 123 back the fluid pit 140 as "effluent". In one or more embodiments, this drilling fluid 130, the influent or inward flow, and the drilling fluid 131, the effluent or upward/outward flow, are part of a continuous circulation of drilling fluid.

As the upward flow of the drilling fluid 131 reaches the surface 103, the flow may be directed into fluid conduit 152, which directs the flow of returning drilling fluid 131 to a fluid reconditioning system 142. The fluid recondition system 142 may comprise any number of devices, such as shakers, screens, and/or wash stations, which are configured to process the drilling fluid 131, for example to remove and/or recover cuttings from the drilling fluid 131 being processed. In one or more embodiments, the fluid reconditioning system 142 can include one or more of desalters, de-sanders, and de-gassing apparatus. The fluid reconditioning system 142 may also process the drilling fluid 131 to refine or alter other properties of the drilling fluid 131, for example to remove dissolved or suspended gasses present in the drilling fluid 131. The fluid reconditioning system 142 may also be configured to add chemicals, such as high dielectric constant muds or clays, conductive nanoparticle suspensions, weighting agents, etc., to the drilling fluid 131 to alter or reinforce various performance properties of the drilling fluid 131 before the drilling fluid 131 is ultimately returned/recirculated to the borehole 110. Upon completion of the processing of the drilling fluid 131 passing through the fluid reconditioning system 142, the drilling fluid 131 may be returned to the fluid pit 140 through a fluid conduit 153. The drilling fluid 131 returned to the fluid pit 140 may then become available for recirculation to the borehole 110 as described above.

An extraction system 144 is fluidly coupled to the circulation of the drilling fluid 131 via a fluid conduit 157 running from the fluid reconditioning system 142 to extract an effluent sample of the drilling fluid 131 that has exited the borehole 110 via the fluid conduit 152. The extraction system 144 is optionally also coupled to the fluid conduit 151 via the fluid conduit 158 to extract an influent sample of the drilling fluid 130 prior to its entering into the drill string 120.

In one or more embodiments, the extraction system 144 includes one or more gas extractors to extract a gas sample from the drilling fluid 131, one or more sampling apparatus to sample or extract the liquids portion of the fluid, or both. The extraction system 144 can sample gas or liquids directly from the fluid reconditioning system 142 or (although not shown) from another point in the flow of drilling fluid 131 from the borehole 110 or the flow of the drilling fluid 130 into the drill string 120.

In addition to the returning drilling fluid being directed to the fluid reconditioning system 142 as described above, in various embodiments of the system 100 a portion of the returning drilling fluid is directed to a sample analysis system (the analysis system 160). The extraction system 144 directs drilling fluid (e.g. effluent drilling fluid 131) extracted or sampled from the fluid recondition system 142 to the analysis system via fluid conduit 159. In one or more embodiments, the extraction system 144 extracts or samples influent drilling fluid 131, e.g., from fluid conduit 151 as shown or, although not shown, from one or more other points in the influent side of the system, e.g. from fluid conduit 150 or from the fluid pit 140.

The analysis system 160 may include an instrumentation 161 and a computer 162. An example of the computer 162 is depicted in FIG. 1, which is further described below. The instrumentation 161 may comprise one or more devices configured to measure and/or analyze one or more chemical and/or physical properties of the drilling fluid provided to the analysis system 160. Illustrative and non-limiting examples of the devices that may be included as part of the instrumentation 161 include one or more gas chromatograph (GC) (e.g., one or more of a gas chromatography-isotope ratio mass spectrometer (GC-IRMS), gas chromatography-infrared isotope ratio analyzer (GC-IR2), dual gas chromatograph with a flame ionization detector (FID), or the like) and one or more mass spectrometer (e.g., one or more of an isotope ratio mass spectrometer (IRMS), magnetic sector mass spectrometer, Time-of-Flight mass spectrometer (TOF-MS), triple quadrupole mass spectrometer (TQMS), tandem mass spectrometer (MS/MS), thermal ionization-mass spectrometer (TIMS), inductively coupled plasma-mass spectrometer (ICP-MS), Spark Source mass spectrometer (SSMS), or the like). In one or more embodiments, instrumentation 161 can further include one or more of a liquid chromatograph, a laser spectrometer, a multivariate optical computing device (e.g. one or more integrated optical element), a nuclear magnetic resonance (NMR) measurement device, a cavity ring-down spectrometer, an electromechanical gas detector, a catalytic gas detector, an infrared gas detector, a cutting analysis tool or system for further analysis of the gas, liquid, and/or solids. In one or more embodiment, the instrumentation 161 also can include one or more temperature sensors for measuring the temperature of the effluent and/or influent samples, and can include one or more pressure sensors to measure the pressure of the effluent and/or influent samples. These sensors or others sensors can also be distributed at different points along the fluid circulation path, such as in the extraction system 144, the pump 141, the BHA 122, the drill string 120, the annulus 114, along any of the fluid conduits 150-159, and/or at another point in the fluid circulation path.

The instrumentation 161 may provide one or more measurements or determined outputs to the computer 162 that can be used as inputs for further analysis, learning, calculation, determination, display, or the like. The fluid samples received by, or continuous measurements obtained by, the analysis system 160, e.g. as inputs to the computer 162, may be correlated with time, depth, and/or other information related to the interaction of the fluid sample with electrical energy emanating from the electrodes of the drill bit 123. For example, a particular sample of drilling fluid may be correlated to a specific time and/or a depth where drilling fluid sample was when the fluid interacted with electrical energy emanating from the electrodes of the drill bit 123. In some embodiments, this correlation is based, at least in part, on the measured rates for flow of the drilling fluid down through the drill string 120 and back up through the annulus 114 over time to determine when the sample of drilling fluid being analyzed interacted with the electrical energy provided by the electrodes of the drill bit 123.

The computer 162, in some embodiments, is integral with one or more of the devices included the instrumentation 161, and/or may be separate computer device(s) that may be communicatively coupled to the devices included in the instrumentation 161. In other examples, the computer 162 may be computing devices, such as personal computers, laptop computers, smartphones, or other devices that allow a user, such as a field technician or an engineer, to enter, observe, and otherwise interact with various software applications providing data reports and control inputs for the measurements and analysis being performed on the drilling fluid by the analysis system 160.

In various embodiments, although not shown, the computer 162 may be communicatively linked with other devices, such as the BHA 122, the pump 141, the extraction system 144, and/or the fluid reconditioning system 142. The communication provided between the computer 162 and other device within the system 100 may be configured to allow the computer 162 to adjust operating parameters, such as but not limited to adjusting the flow rates of drilling fluid provided to the drill string 120, control over the positioning of the drill string 120 with the borehole 110, and control over the operating parameters associated with the electrical generation and application of electrical power being performed by the bottom hole assembly 122.

Communications from the computer 162 may also be used to gather information provided by the fluid reconditioning system 142, and/or to provide feedback to the fluid reconditioning system 142 to control the processes being performed on the returning drilling fluid by the fluid reconditioning system 142.

The analysis system 160 and the extraction system 144 (from the extracted samples from the influent 130 and the effluent 131) can output one or more compositions of the drilling fluid, one or more compositions of the formation fluid, and/or one or more isotope ratios. For example, the extracted sample from the influent 130 can be used as a baseline to determine the contribution of the formation fluid and/or a downhole reaction at the drill bit to the composition of the effluent.

The analysis system 160 may determine various parameters related to the formation 113, and/or various parameters related to the operation of the pulse power drilling assembly, based on measurements and/or analysis performed to determine various chemical and/or physical properties present in the drilling fluid that has been exposed to or that has otherwise interacted/reacted with the electrical energy provided by the electrodes of the drill bit 123. Further, various operating parameters, such as electrical parameters, associated with the discharge of the electrical energy from the electrodes of the drill bit 123 within borehole 110, may be measured and analyzed to derive data and make determinations about various parameters associated with the formation 113, parameters associated with properties of the drilling fluid, parameters associated with the operating parameters of the BHA 122, and/or parameters associated with the operating parameters of the PPD assembly 126.

In various embodiments, the system 100 may include the analysis system 160 having a communication link, illustratively represented by a lightning bolt 164, configured to provide communications between the analysis system 160 and one or more remote computer systems 163. The remote computer systems 163 may be configured to provide any of the data functions associated with and/or the analysis function described above that may be associated with the drilling fluid as provided by the analysis system 160. In various embodiments, the remote computer systems 163 may including storage devices, such as data storage disks, configured to store the data being generated by the analysis being performed by the analysis system 160. In various embodiments, the remote computer system 163 may include display devices, such as computer monitors, that allow users at remote location, i.e., locations away from the location where the system 100 is physically located, to visually see and interact with the visual representations of the data being provided by the analysis system 160. In various examples, control inputs, as described above, may be provided via user input provided to the remote computer systems 163 and communicated to the analysis system 160 for the purpose of controlling one or more of the operating parameters associated with system 100.

In some embodiments of the system 100, the BHA 122 includes a sampling tool 124. The sampling tool 124 may be located within the housing of the BHA 122. The sampling tool 124 may be coupled to the annulus 114 through the port 125, wherein the port 125 provides a fluid communication passageway between the annulus 114 and the sampling tool 124. In various embodiments, the port 125 may be used to collect a sample of drilling fluid, such as the drilling fluid illustratively represented by dashed-line arrows 131. The sample of collected drilling fluid may be provided to the instrumentation 161, where one or more measurements and/or further analysis of the drilling fluid may be performed by the sampling tool. Measurements made, e.g., from one or more pressure or temperature sensors and/or a multivariate optical computing device, and/or data collected from the analysis of the samples of drilling fluid collected through the port 125 may be communicated through a communication link, e.g., via wired (like a wireline or wired pipe) or wireless telemetry (like mud pulse, acoustic, or electromagnetic telemetry) to the surface, and optionally to the analysis system 160. In the alternative or in parallel with the above, the sample of drilling fluid collected through the port 125 may be contained, for example bottled, and then transported back to the surface with the BHA 122. Any samples of drilling fluid collected via the port 125 may be data stamped with information indicating the time, depth, and/or other information associated with the collection of the fluid sample.

Figure 2A:
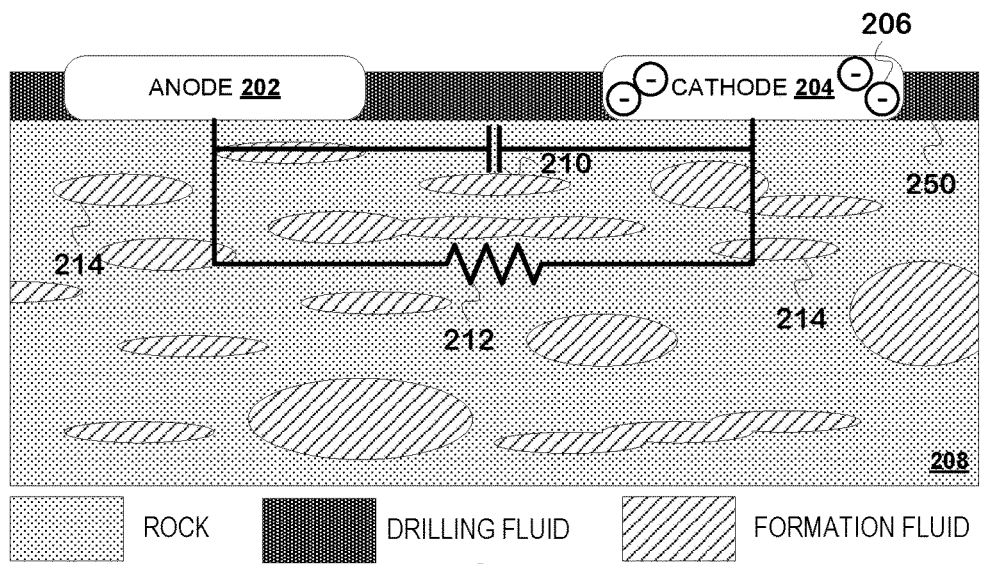
FIG. 2A depicts electrodes of a pulse power drill string at the bottom of a wellbore prior to emission of a pulse into the formation, according to one or more embodiments.
Figure 2B:
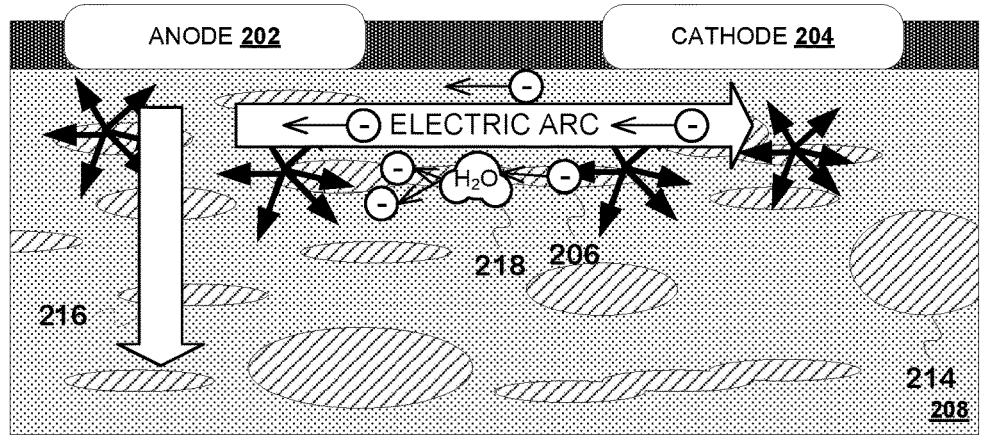
FIG. 2B depicts the electrodes of a pulse power drill string of FIG. 2A during emission of a pulse into the formation, according to one or more embodiments.
Figure 2C:
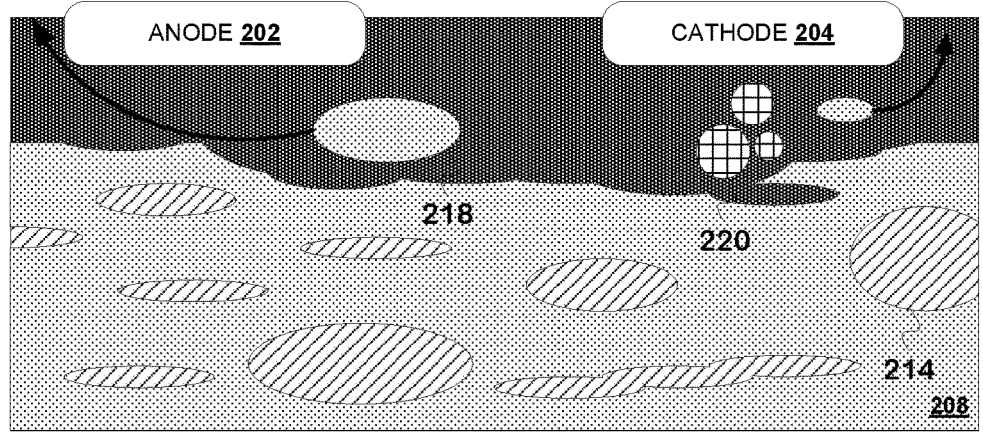
FIG. 2C depicts electrodes of a pulse power drill string at the bottom of a wellbore after emission of a pulse into the formation, according to one or more embodiments.

FIGS. 2A-2C depict electrodes of a pulse power drill string at the bottom of a wellbore at three different points in time relative to the emission of a pulse into the formation, according to one or more embodiments. FIG. 2A depicts electrodes of a pulse power drill string at the bottom of a wellbore prior to emission of a pulse into the formation, according to some embodiments. In this example, a drill bit includes electrodes depicted as an anode 202 and a cathode 204. The anode 202 and the cathode 204 can be examples of the electrodes within the drill bit 123 of the drill string 120 of FIG. 1.

In pulse power drilling, the anode 202 and the cathode 204 (when not performing off-bottom analysis) can rest along a bottom 250 of the wellbore in contact with a formation 208. The formation 208 includes a number of pore spaces 214 having formation fluid. One or more of the electrodes can be charged by portions of the drill string as described above. This charging can induce charge carriers at the electrode formation interface—either electrons or holes which are theoretical charge carriers representing the absence of electrons. For simplicity, only electrons 206 are shown.

The dielectric between the anode and cathode can be comprised of the formation rock or stone, the formation fluid in the pores of the rock strata, and the drilling fluid pumped downhole. The dielectric, before the plasma is applied, can be approximated as a resistor 212 in parallel (or alternatively in series) with a capacitor 210, where the dielectric strength can be a function of porosity, permeability, formation type, formation fluid composition, and drilling fluid composition.

FIG. 2B depicts the electrodes of a pulse power drill string of FIG. 2A during emission of a pulse into the formation, according to some embodiments. As shown in FIG. 2B, a plasma discharge into the formation 208 can result in vaporization of the fluid in the pore spaces 214, which causes expansion of the liquid in the pores as it is converted to a high-pressure vapor or gas, and leads to destruction of the rock. Formations without pore spaces, or with small, impermeable pore space, are also susceptible to pulse power drilling. In such dry formations, the plasma discharge occurs through the rock itself, which then suffers from dielectric breakdown, creating fissures and fault lines along the current path. Vaporization of fluid is a faster pulse power drilling method, but both mechanisms can be active in the same rock at the same time.

At the pressure and temperature of a wellbore, the ideal gas law is not a good approximate of the volume of a gas. The gas volume for hydrocarbons is modeled using the Wilson model, or another thermodynamically complex model or approximation. The volume of gas (such as $H_2$, $CO_2$, etc.) generated downhole—but not the volume of vapor generated (such as steam)—can be calculated from the volume of gas evolved at the surface. The volume of gas detected at the surface can be converted to a molar amount via the ideal gas law (see Equation 1 below).

$$PV = nRT \tag{1}$$

Where P is pressure, V is volume, n is the number of moles of the gas, R is the ideal or universal gas law constant and T is temperature in Kelvin. At high temperatures and pressures downhole, the ideal gas law approximation can be inaccurate and gas volume is calculated using Wilson's equation for a multi-component fluid (see Equation 2 below) or a similar equation.

$$\ln[\gamma_k] = 1 - \ln\left[\sum_{j=1}^{n}(x_j A_{kj})\right] - \sum_{i=1}^{n}\left[\frac{x_i A_{ik}}{\sum_{j=1}^{n}(x_i A_{ij})}\right] \tag{2}$$

Wilson's model determines the liquid phase activity coefficient $\gamma$ for component k as a function of the molar fraction $x_n$ of each of n components, where $A_{ij}$, $A_{ji}$ are the Wilson coefficients for the binary pair of components i and j. The liquid phase activity coefficient $\gamma$ is related to the partial pressure of each compound in the fluid via Raoult's law (Equation 3) or a similar approximation.

$$p_k = x_k \gamma_k p_k^\sigma \tag{3}$$

In Raoult's law, $p_k^\sigma$ is the saturation pressure or vapor pressure of the undiluted component (i.e. of each component in its pure form).

Current flows from the anode 202 to the cathode 204, which corresponds to a flow of the electrons 206 from the cathode 204 to the anode 202. The electrons 206 are injected from the cathode 204 into the dielectric under the influence of the electric field generated between the anode 202 and the cathode 204. The electric field can be approximated for a parallel plate capacitor as given by Equation 4 below:

$$E = \frac{\Delta V}{d} \tag{4}$$

Where E is the electric field (in Volts (V) per meter or another unit) for a parallel plate capacitor approximation for electrodes separated by a distance d and at a voltage difference of $\Delta V$. The electric field between the anode 202 and the cathode 204 is not uniform if the formation is not microscopically uniform, which is true for any formation strata with fluid filled pores. The average electric field can be approximated as shown in Equation 5:

$$\overline{E} \sim \frac{\Delta V}{d} \tag{5}$$

Where $\overline{E}$ is the average electric field in the dielectric between the electrodes, $\Delta V$ is the voltage drop from anode to cathode (or between the electrodes, generally) and d is the separation distance between the electrodes.

The electrons 206 accelerate in the electric field in the dielectric until they experience a collision with particle. The collision of charged particles in a plasma can generate an avalanche multiplication current, as described by Townsend (and further explained in reference to FIGS. 5A-5B). Similarly charged particles repel each other, but neutral and opposite polarity particles experience collisions at appreciable rates. The electron 206 collides with water molecule 218 leading to the generation of an additional electron. This collision would be governed by the hydroxide ion chemical formation shown in Equation 6 below:

$$e^- + H_2O \leftrightarrow \tfrac{1}{2}H_2 + HO^- + 2e^- \tag{6}$$

where $e^-$ represents electrons and $HO^-$ represents hydroxide ions. Another reaction pathway generates hydroxyl radicals but no additional electrons as shown in Equation 7:

$$e^- + H_2O \leftrightarrow \tfrac{1}{2}H_2 + HO\cdot + e^- \tag{7}$$

Where HO. represents a neutral hydroxyl radical, and where free radicals or radicals are electrically neutral molecules with at least one unpaired electron and can be very reactive. In this way, the plasma generates high energy particle collisions that produce chemical reactions downhole.

A portion of the electric current travels not between the cathode and anode, but out into the formation as plasma sparking. The portion of the plasma power that generates a plasma spark 216 or sparking does not lead to appreciable current transfer between the anode and cathode—although current may flow to ground or into the formation. Sparks of plasma typically have higher plasma temperatures than arcs of plasma, as will be discussed in more detail below in reference to FIGS. 5A-5B, which affects the types of products generated and their reaction rates. Plasma sparks also vaporize fluid, breakdown rock, and contribute to drilling. Plasma sparks can be undesirable because they unevenly form at one electrode, instead of dissipating power equally between both anode and cathode. However, plasma sparks may be useful in directionally modifying drilling such as when turning the wellbore is required.

FIG. 2C depicts electrodes of a pulse power drill string at the bottom of a wellbore after emission of a pulse into the formation, according to some embodiments. The vaporization of the formation fluid generates expansive gases. As the plasma is quenched, the gasses are dissolved into the high-temperature and high-pressure drilling fluid. The formation solids (rocks or particulates), having been broken into smaller pieces by the plasma, are carried away as cuttings by the drilling fluid. The destruction of the solid matrix frees fluid 220 formerly trapped in pore spaces within the rock. However, the fluid 220 from the regions where plasma was generated is no longer formation fluid but rather plasma reaction products. This too travels to the surface dissolved in the drilling fluid to be analyzed and categorized.

Example Operations

Figure 6:
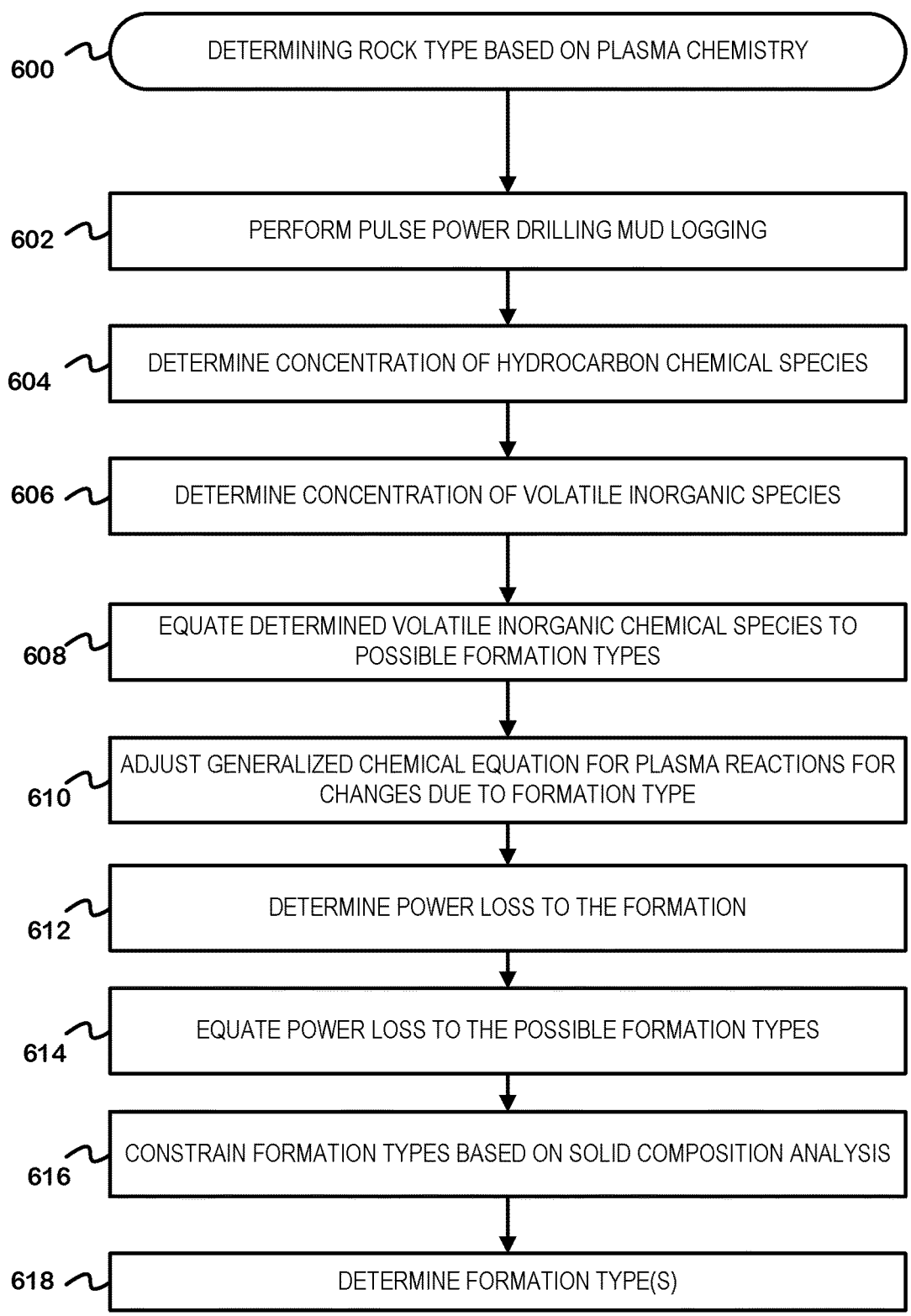
FIG. 6 depicts a flowchart of example operations for determining rock type based on plasma chemistry, according to one or more embodiments.
Figure 7:
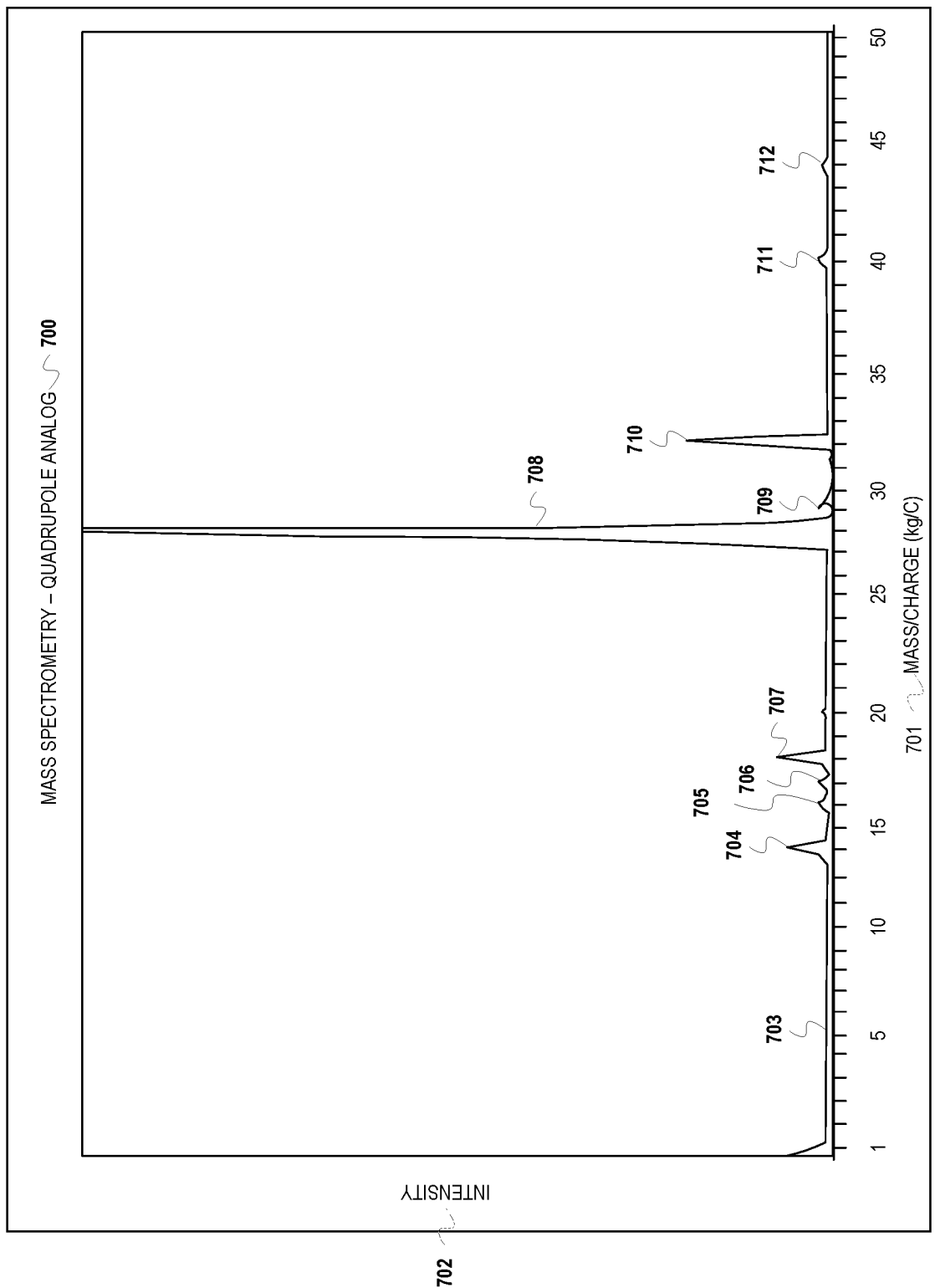
FIG. 7 depicts an example mass spectrometry graph, according to one or more embodiments.
Figure 8:
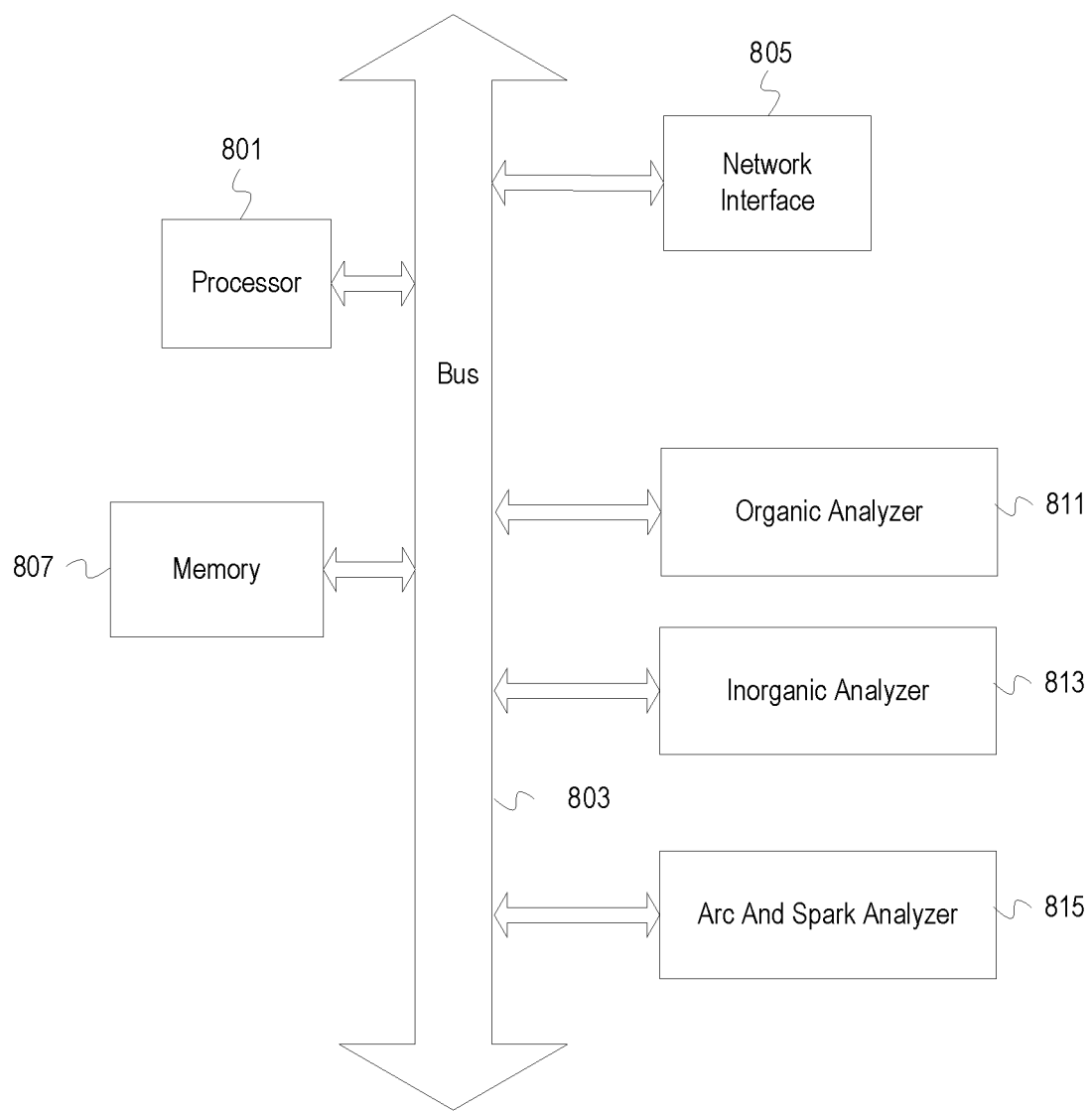
FIG. 8 depicts an example computer, according to one or more embodiments.

Example operations are now described. The following description of example operations include Subsections A-B. Subsection A includes a description of example pulse power mud logging operations (FIGS. 3A-3B and 4-5). Subsection B includes a description of an example of deriving formation rock type based on plasma chemistry (FIG. 6-8).

A. Example Pulse Power Mud Logging Operations

Figure 3A:
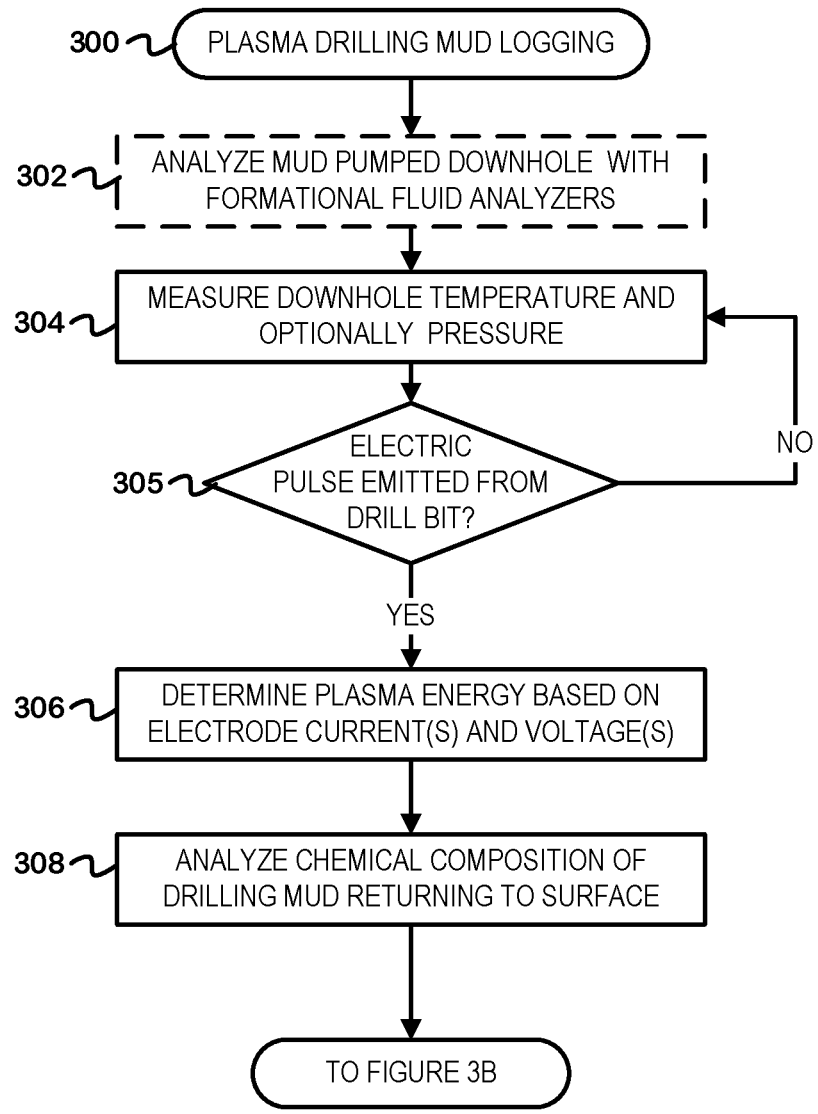
FIGS. 3A-3B depict a flowchart of example operations for pulse power mud logging, according to one or more embodiments.
Figure 3B:
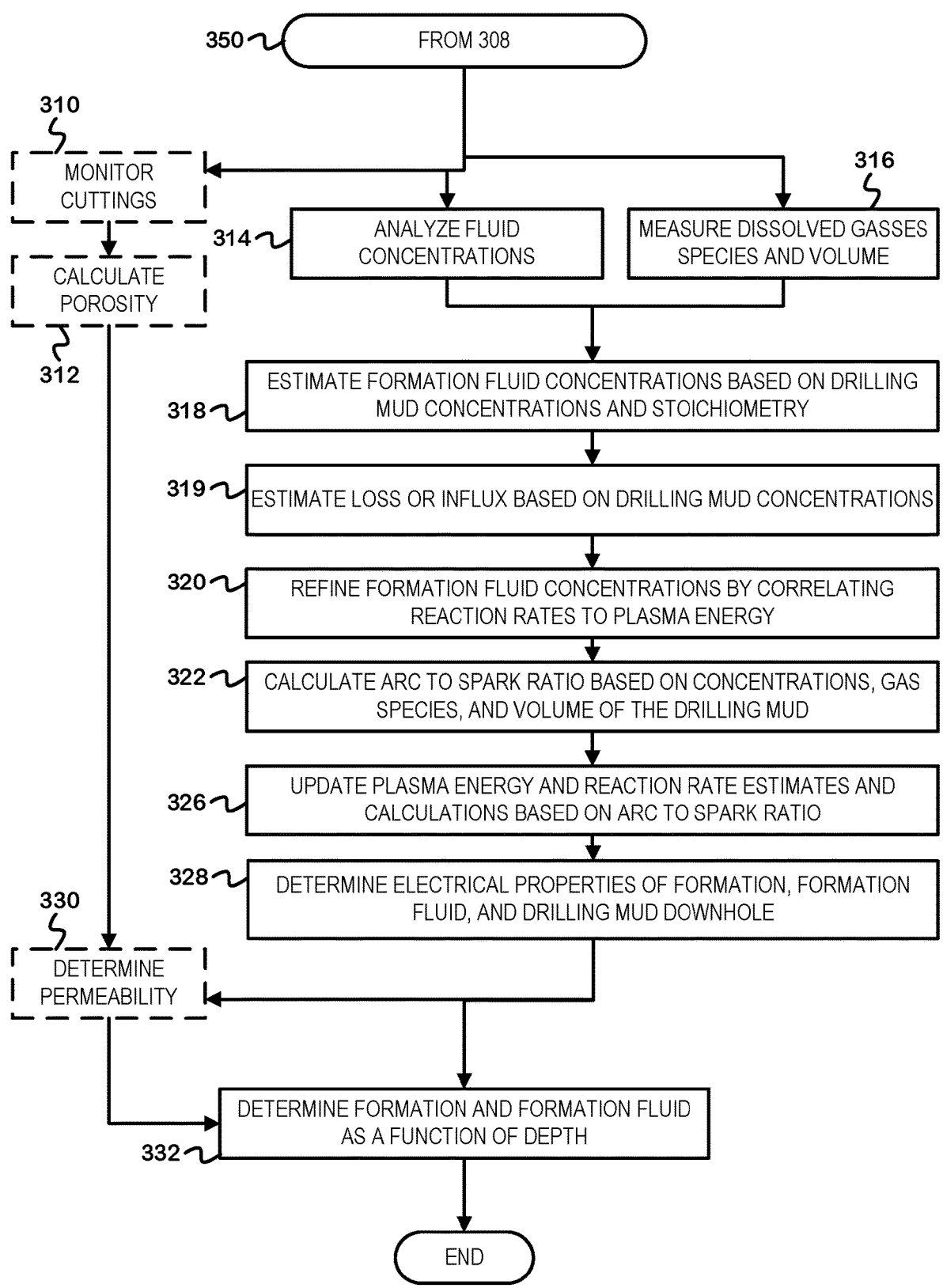

FIGS. 3A-3B depict a flowchart of example operations for pulse power mud logging, according to one or more embodiments. A flowchart 300 of FIG. 3A and a flowchart 350 of FIG. 3B includes operations described as being performed by the pulse power drilling and mud logging system for consistency with the earlier description. However, program code naming, organization, and deployment can vary due to arbitrary programmer choice, programming language(s), platform, etc. The flowchart 300 includes blocks 302, and the flowchart 350 includes blocks 310, 312, and 330 depicted with broken lines. Such blocks represent examples of operations that can be optionally performed. This depiction of the blocks of the flowchart 300 and the flowchart 350 should not be interpreted as requiring operations in the blocks depicted with solid lines, as one or more other operations in the solid blocks can be optional also. Operations of the flowchart 300 start at block 302, while operations of the flowchart 350 continue at blocks 310, 314, and 316 from block 309 of the flowchart 300.

FIGS. 3A-3B include operations related to plasma parameters, mud logging, and drilling optimization for an example pulse power drilling system. Pulse power mud logging includes several methods for determination of formation fluid and generation of mud logging records based on both downhole drilling measurements and on surface fluid characterization. The relationship between the chemical composition of drilling mud returned to the surface (including cuttings and solids, dissolved gasses, and liquid hydrocarbons) and the formation fluids entering the wellbore downhole can be complicated by the plasma pulses created while drilling and the destructive reactions thereby engendered. By iteratively or sequentially solving a number of groups of equations and balances, the total degrees of freedom of the system can be reduced so that the problem is solvable—that is the formation fluid concentration can be determined or back calculated. The determination steps are shown here in a particular order, which is illustrative only, and it should be noted that each balance, set of equations, or determination can be applied in any order, including stepwise or iteratively.

At block 302, drilling mud to be pumped downhole is analyzed with formational fluid analyzers. For example, with reference to FIG. 1, the instrumentation 161 can perform this analysis as the mud enters the wellbore to be pumped downhole. The concentration of hydrocarbon species in the drilling mud can measured using analyzers and detectors similar to those used to analyze the chemical composition of the drilling mud returned to the surface in block 308 (as further described below). Optionally, the same analyzers can be used to determine the composition of the drilling mud returned to the surface and the drilling mud entering the wellbore. Because the drilling mud circulates through the wellbore, chemical reactions downhole cause drift in the mud's chemical composition. Measuring the drilling mud's chemical composition as the mud enters the wellbore allows the mud logging system to account for the initial concentration of hydrocarbons and water (as shown in Equation 8) and determine the change in concentration for each iteration through the wellbore precisely.

$$\Delta P = [P]_{product} = [P]_{exiting\ wellbore} - [P]_{entering\ wellbore} \quad (8)$$

Where P is an example product molecule or species, [P] is a concentration of the example product and can be normalized for flow rate, rate (as of time), or volumetrically, and the concentration of P can change as a function of time of as a function of the total volume of drilling mud. ΔP represents the total change in product in the drilling fluid due to one cycle through the wellbore and corresponding exposure to plasma.

In some embodiments, if the drilling mud is not analyzed as it enters the wellbore, the drilling mud composition is assumed from the chemical composition of the drilling mud as it reaches the surface, which is determined at blocks 308 and 309, minus the concentration of gasses, which are removed from the drilling fluid before it enters the mud pit or another storage unit (as further described below in reference to block 316).

At block 304, temperature and, optionally, pressure downhole are measured. For example, with reference to FIG. 1, the computer 162 can perform this operation. The temperature of the drilling fluid can affect the reaction rate constants and plasma parameters, such as breakdown voltage, dielectric constant, etc. The mud logging system can correlate the downhole temperature to drilling mud analyzed at the surface by adjusting for drilling mud pumping speed and drilling speed.

At block 305, a determination is made of whether an electric pulse is emitted from the drill bit. As described above, the electrodes in the drill bit periodically emit an electric pulse to drill the borehole. For example, with reference to FIG. 1, the computer 162 can determine when the electric pulse is emitted. If there is no electric pulse emitted, operations of the flowchart 300 remain at block 304. Optionally, flow can continue to block 308 in the absence of a detected pulse and perform mud logging calculations based on possible plasma reaction products in drilling mud that may result from previous reactions. The drilling mud circulation time causes a temporal mismatch between when the pulse is detected and when the products are detected and analyzed at block 308. Otherwise, operations of the flowchart 300 continue at block 306.

At block 306, the plasma energy is determined based on electrode current(s) and voltage(s). For example, with reference to FIG. 1, the computer 162 can make this determination. The plasma energy can be determined based on anode and cathode current and voltage of the drill bit. Plasma power calculations can assume that power added to the system is approximately equal to the plasma power, or can account for power lost to the formation, heat of vaporization, etc.

In a closed-loop system where electrons are neither created nor destroyed, the current flowing through the system can be determined based on current measured at the anode (the anode current) and at the cathode (the cathode current) as given by Kirchhoff's current law. Kirchhoff's current law does not apply in a plasma, as the acceleration of electrons in the electric field of the plasma can cause Townsend avalanche multiplication, as will be discussed later. Electrons and positive ions can be created in the plasma. However, the electrons and positive ions can recombine when the plasma generation ends to form neutral molecules which are the reaction products. Once initiated, the plasma itself can be considered a conductor of infinite conductivity or zero resistance.

When the anode and cathode currents are equal and the plasma is quenched, no current flows into the formation or away to ground. If the anode and cathode currents are unequal, the difference can represent current lost to the formation or current created by the electrons and ions generated by the plasma. Current lost to the formation can be approximated as current lost to ground where the formation functions as a grounding electron sink. The relationship between anode, cathode, and formation current is then given by Equation 9 below:

$$I_{anode} = I_{cathode} + I_{formation} + I_{plasma} \quad (9)$$

Where $I_{anode}$ represents the current flowing out of the anode, $I_{cathode}$ represents the current flowing into the cathode, and $I_{plasma}$ represents any additional current generated by the plasma. $I_{formation}$ represents any current lost to the formation or otherwise away from the anode or cathode, or another electrode. For pulse power drilling in a wellbore, the formation current is approximately the ground current as shown in Equation 10, below:

$$I_{formation} \approx I_{ground} \quad (10)$$

Where $I_{ground}$ is the current lost to or gain from ground, which is approximately the formation or earth acting as an electron sink. $I_{formation}$ and $I_{ground}$ may or may not be measurable.

Plasma can form in the combination of drilling mud, rock or formation, and formation fluid when the applied voltage is above the dielectric breakdown voltage of that combination, for the downhole temperature and pressure. At voltages above breakdown, electrons separate from molecules, generating positive ions. The electrons have much smaller mass than the positive ions and accelerate in the electric field towards the anode. In a low-pressure plasma, the mean free path of the electrons can be long, and the electrons may experience significant acceleration. Very fast electrons can generate additional electrons through the Townsend avalanche multiplication when they collide with positive ions or neutral molecules on their way to the anode. In a high-pressure plasma where free electrons can be drawn from ground, such as found when drilling in a formation, the mean free path of the electron can be so short that avalanche electron multiplication is negligible. In either case, the increase in current generated by the plasma is encompassed by the term $I_{plasma}$.

The value of the Townsend current is given by Equations 11-12, below:

$$I = I_0 e^{\alpha_n d} \quad (11)$$

$$I = I_0 \frac{(\alpha_n - \alpha_p)\text{Exp}[(\alpha_n - \alpha_p)d]}{\alpha_n - \alpha_p \text{Exp}[(\alpha_n - \alpha_p)d]} \cong I_0 \frac{\text{Exp}[\alpha_n d]}{1 - \frac{\alpha_p}{\alpha_n} \text{Exp}[\alpha_n d]} \quad (12)$$

$I_0$ represents current generated at the cathode surface (which can be approximated as $I_0 = I_{cathode}$), $\alpha_n$ is the first Townsend ionization coefficient, $\alpha_p$ is the secondary ionization Townsend coefficient, and d is the distance between the anode and cathode of a parallel plate capacitive discharge. $\alpha_n$ represents the number of particle pairs generated by a negatively charged particle (anion or electron) per unit length, where such a negative particle is moving from cathode to anode. $\alpha_p$ represents the number of charged particle pairs generated per unit length by a cation, during its collisions while moving from anode to cathode. Equation 11 considers only electrons traveling at speeds sufficient to cause ionization collisions (i.e. a non-thermal plasma), while Equation 12 also considers positive ion (i.e. cation) traveling fast enough to impart ionization energy to neutral particles (i.e. a thermal plasma).

For a downhole plasma where d is known, the plasma current can be determined or estimated based on an exponential fit to the anode and cathode currents. The exponential portion of the increase in current during the lifetime of the plasma results from the avalanche multiplication in the plasma. Current lost to the formation or ground should exhibit only minimal capacitive or inductive charging (i.e. current that depend exponentially on time) and is predominantly resistive in nature and therefore distinguishable from the plasma current.

A plasma arc can be defined as a plasma generated between the cathode and anode along with a significant transfer of current. A plasma spark can be defined as a non-directional or isotropic plasma without a directional current transfer. Plasma arcs between the cathode and anode and through the dielectric that can include the formation fluid, formation, and drilling mud, but can also arc between either of the electrodes and the formation or subsections of the formation. Plasma arcs can be detectable from their effect on the cathode and anode currents. Plasma sparks, where electrons are not accelerated appreciably between the cathode and anode, can be detectable via their drawn down of voltage (or power) from the anode and cathode. Plasma arc and plasma sparks can have fundamentally different plasma temperatures and geometries, which can lead to different high-energy transition states and chemical reactions, which will be discussed in more detail below in reference to FIGS. 5A-5B. For pulse power generation, the determination of a ratio between a plasma arc and plasma sparking can be estimated via electrical measurements and further or iteratively refined based on concentration of chemical products and determination of reaction rates from surface stoichiometric analysis.

The power added to the system can be determined by the current flowing through and the voltage drop over the system. If the cathode and the formation are at 0 volts (V) or ground, then the total power added to the system is given by the anode current multiplied by the anode voltage, as given by Equation 13 below:

$$P = I_{anode} V_{anode} \quad (13)$$

Where P represents power in this instance (in units of Watts or equivalent), $I_{anode}$ is the current flow at the anode electrode, and $V_{anode}$ is the electric potential (or voltage) of the anode. Equation 14 describes the general relationship between power, current, and voltage for electric systems.

$$P = IV \quad (14)$$

Where power P is equal to current I multiplied by voltage V.

If the cathode is not also a ground source or if information about the current and voltage at the cathode is known, then the power added into the system is given by the approximation of Equation 15, below.

$$P = I_{anode} V_{anode} - I_{cathode} V_{cathode} \quad (15)$$

Where $I_{cathode}$ is the current flow at the cathode electrode and $V_{cathode}$ is the electric potential of the cathode (which is the same as its voltage).

The plasma power, i.e. the power consumed to generate the plasma, can be assumed to account for the power input into the system. The plasma power approximation can be iteratively updated as a function of time. For a system where only the current at one electrode or the total power added to the system is known, the plasma power can be correlated to reaction rates, activation energies, and product concentrations instead of directly calculated. Pulse power discharges of similar power can be assumed to have similar properties, including spark vs. arc ratio, reaction rates, etc.

The power balance represents an instantaneous energy balance, where power is energy per unit time. The total energy balance of the system also provides information about the plasma power. For a plasma pulse of known duration, energy balance equations can be substituted for power balance equations. In this case, the total energy of formation of the products relates to the power or energy of the plasma. If products and product concentrations of the chemical reactions are known, a total chemical energy balance can be determined based on the enthalpy of formation of the product species and the temperature and pressure at which the reactions occur.

In the total energy balance, the total energy added to the fluid by the plasma also accounts for changes in temperature and pressure within the fluid. The plasma can result in vaporized fluids, such as those within pores in the formation rock, entering the drilling fluid as gasses. The energy absorbed by the physical state change can be calculated from the heat of vaporization and the concentration of the gaseous products. Other fluids experience temperature changes, where the energy occupied by heating such fluids can be calculated from the specific heat of capacity multiplied by the temperature change. As fluid in the wellbore heat and/or vaporize, pressure changes can occur. The increase in pressure can account for additional energy in the system stored as increased enthalpy.

In either case, the power or energy of a given plasma pulse is correlated to the products of such a reaction which reach the surface at a time delayed from the reaction. Traditional mud logging correlates drilling mud chemical constituents to the depth at which they entered the borehole. Pulse plasma mud logging additionally correlates drilling mud chemical constituents to a specific reaction time, current, and voltage in order to back calculate formation fluid properties. The lag between pulse power reaction and drilling mud arrival at the surface is determined based on drilling rate, circulation rate, and drill depth.

For a DC plasma, current will vary with time, even during the plasma pulse itself. Before the plasma is generated, the current is low and the resistivity between dielectric between the anode and cathode (which can be modeled as the drilling fluid resistivity, formation rock resistivity, and formation fluid resistivity in parallel) is high. The voltage between the anode and cathode builds as the cathode is charged until the voltage applied over the dielectric is greater than the dielectric's breakdown voltage and a plasma is generated.

The resistivity of the plasma is low, and it can be modeled as a conductor of zero resistivity between the anode and cathode. If there are available free electrons in the system, an approximation applicable when electrons can be drawn from ground or stripped from water molecules in the drilling fluid, the current generated by the plasma can be estimated by the Townsend discharge equations (Equations 11-12, above) or determined via Kirchhoff's law from the other known currents.

A plasma is overall electrically neutral—the electrons generated by the avalanche cascade reactions are compensated by free electrons absorbed from ground or generated by ionization. The number of positive ions (cations) and electrons (where the contribution of anions can be approximated as $n_a \approx 0$) are approximately equal. The degree or fraction of ionization for a plasma is given by Equation 16, below:

$$f_i = \frac{n_e}{(n_e + n_0)} \tag{16}$$

Where $n_e$ is the number of electrons, $n_0$ is the number of neutral atoms or molecules, and $f_i$ is the ionization fraction.

Each particle in the plasma has a kinetic energy. Because there are so many electrons, ions, and atoms or molecules, the kinetic energy is oven expressed as an energy distribution or particle temperature. The plasma temperature of electrons is given in Equation 17, below for a Maxwell-Boltzmann distribution.

$$T_e = \frac{2}{3} \frac{\langle E \rangle}{k_B} \tag{17}$$

Where $T_e$ is the electron temperature, $\langle E \rangle$ is the average plasma energy, and $k_B$ is the Boltzmann constant. The Maxwell-Boltzmann probability distribution describes a distribution of particle kinetic energy or speeds at thermodynamic equilibrium and is commonly used in statistical mechanics to approximate particle velocities and interactions as a function of temperature. Electron temperature is a fundamental measure of the energy of the electrons in a plasma and is used to calculate other plasma properties, such as collision rate, mean free path, etc., and is often given in units of Kelvin (K) or electron Volts (eV).

Plasmas are classified as either thermal, where anions, cations, and electrons have similar kinetic energy (i.e. are in thermal equilibrium) and non-thermal, where electrons alone have kinetic energy proportional to the plasma energy. The first plasma of the plasma pulses generated is generally a non-thermal plasma where the electrons of the plasma have a higher kinetic energy than the ions and molecules of the plasma. Thermal plasmas are generated from non-thermal plasmas as energy added to the plasma in the form of current and voltage increased the kinetic energy of the charged particles until they reach the same kinetic energy as the electrons. Thermal plasma are more common in alternating current (AC) and long lifetime plasmas, but can occur in DC plasmas and pulsed plasmas where the dielectric is sufficiently heated before the plasma is initiated (either by environmental heating or by previous plasma produced through the same dielectric). For a thermal plasma approximation as shown in Equation 18 below:

$$T_a = T_c \approx T_h = T_e \tag{18}$$

Where particle temperatures include anion temperature $T_a$ and cation temperature $T_c$. Both anions and cations are heavier (i.e. more massive) then electrons and are approximately equal to a heavy particle kinetic energy $T_h$. Energy is added to the motion of the charged particles by the electric field based on magnitude of the charge not polarity.

Reaction rate constants for products generated in a plasma or at the quenching of the plasma depend on both the temperature of the plasma—electron temperature and heavy particle temperature—and upon the total ionization. By determining the reaction rates based on chemical concentrations in the drilling mud, the plasma temperatures can be monitored.

The average plasma energy $\langle E \rangle$ is related to both the energy applied to the plasma and to the electron temperature. The plasma power is related to the potential energy difference over the plasma (in Volts) times the work of moving the current (in Amperes) through the electric field. Power and energy are related, where power is energy per unit time (such as Watts), as shown in Equations 19 and 20 below.

$$\text{Power} = \frac{\text{Energy}}{\text{Time}} = \frac{\langle E \rangle}{\Delta t} \tag{19}$$

$$\text{Power} = \frac{\partial}{\partial t} \text{Energy} = \frac{\partial}{\partial t} \langle E \rangle \tag{20}$$

Where power can also be represented as P, energy as E, average energy as $\langle E \rangle$, and where t is time.

Reaction rates are a function of plasma temperature (which is a measurement of plasma energy), which means that plasma temperature can be calculated or correlated to measured reaction rates. Plasma power can be approximated from the power added to the system, and from the approximate plasma power and the plasma duration and an average plasma energy can be calculated. By comparing these two measures of plasma energy, the energy system can be checked for energy loss (i.e. energy lost to the formation can be detected). Either method can be used to approximate the other.

At block 308, the chemical composition of the drilling mud returning to the surface is analyzed. For example, with reference to FIG. 1, the instrumentation 161 can perform the analysis. The drilling mud can include both chemical reaction products and formation fluid acquired downhole, as well as solids in the form of formation cuttings. The drilling mud can be separated by phase, where cuttings and other solids (such as debris from the surface like gloves, bolts, etc.) are removed. To illustrate, a shaker and/or screen can receive the drilling mud from downhole and separate the cuttings and other solids from the drilling mud. For example, with reference to FIG. 1, the fluid recondition system 142 can perform this separation. The instrumentation 161 analyzes the solids at block 310 of FIG. 3B. The drilling mud logging system separates dissolved gasses via low-temperature or low-pressure separation from the hydrocarbon liquids. The gasses are then analyzed at block 316 of FIG. 3B, before being fed to a flare for disposal or safely stored. A portion of the cleaned drilling mud fluid can be diverted to allow the instrumentation 161 to analyze this fluid for chemical composition at block 314 of FIG. 3B.

At block 309, the chemical concentration of the reaction product is determined. For example, with reference to FIG. 1, the computer 162 can make this determination based on the instrumentation 161 or the analysis system 160. The chemical concentration can be measured in weight per volume (such as grams per liter g/L), moles per volume (such as moles per liter mol/L), weight percent (such as nanograms per milliliter ng/mL), parts per million (ppm), mole percent or mole fraction (such as mol compound/mol total or mol %), etc. The chemical concentration can be measured for a specific amount of drilling fluid, or as a function of drilling rate or time.

At block 310, the cuttings can be analyzed to determine the volume of rock returned to the surface. For example, with reference to FIG. 1, the instrumentation 161 can analyze the cuttings. Methods of cutting measurement include optical scanning and image processing to determine particle size distribution, weighing of cuttings, and calculating volume based on a measured density (where the density is measured using a core sample or periodically for each formation layer), or via a large bore Coriolis density meter.

At block 312, porosity is determined based on the measurement of cuttings that occurred at block 310. For example, with reference to FIG. 1, the computer 162 can make this determination. The computer 162 can reconstruct the total volume of rock removed from the formation. The computer 162 can also compare that volume as a function of time to the drilling rate to determine the ratio of rock to pore space in the formation layer being drilled. The pore fraction ø is given by Equation 21:

$$\phi = \frac{V_v}{V_T} \tag{21}$$

Where the pore fraction ϕ is a dimensionless number representing the portion of the rock volume occupied by pores and where $V_T$ is the total volume and $V_V$ is the void volume. Void volume can be correlated to pore shape, pore size, and pore throat size (where pore throat size is a determining factor in permeability).

Porosity and permeability of the formation information can be determined in traditional mud logging from information about changes in the volume of drilling fluid and from measurements on the size and volume of cuttings. The plasma reaction downhole in pulse power drilling converts a portion of the drilling fluid and formation fluid to gas. Once the mass balance of the reaction is determined, the original volume of fluid downhole is determined. Based on the volume calculation, the drilling mud volume is further subtracted and the remaining volume is a measure of formation fluid volume as a function of drilling depth. By accounting for formation fluid volume per unit of depth drilled, the percentage of formation rock that constitutes formation fluid space is calculated as a measure of porosity. The volume of rock fragments measured at the surface and the calculate pore volume equal the total volume drilled, as a function of time. Each method can therefore function as a check on the value of the other.

At block 330, permeability is determined based on porosity and electrical characteristics of plasma discharge, as will be discussed later. For example, with reference to FIG. 1, the computer 162 can make this determination.

At block 314, the chemical composition of the fluid is determined. For example, with reference to FIG. 1, the computer 162 can make this determination. The chemical composition of the fluid can include various hydrocarbons and water. The computer 162 can determine which chemicals are present and their concentration levels. The computer 162 can make this determination using the instrumentation 161 that can include application of gas chromatography, liquid chromatography, mass spectrometry, absorption or emission spectrometry, nuclear magnetic resonance spectrometry (NMR), or the like.

At block 316, the molar concentrations of gasses produced by the plasma reaction is determined. For example, with reference to FIG. 1, the computer 162 can make this determination. The molar amount of gas produced can be determined based on the volume of gas detected at the surface, using the ideal gas law where each mole of gas corresponds to 22.4 at standard temperature and pressure (STP).

At block 318, the formation fluid concentrations are determined based on the concentrations of species in the drilling mud and estimated stoichiometry of a chemical reaction. This chemical reaction may be more specifically a dehydrogenation reaction, where hydrogen gas is produces from hydrocarbons as they form more saturated bonds (i.e. more double bonds). For example, with reference to FIG. 1, the computer 162 can perform this estimation. The computer 162 can determine the change in drilling mud species concentration by subtracting the concentrations of species found in the drilling mud pumped downhole (from block 302, 308, or 309 depending on drilling rig set up). Based on the change in concentration that corresponds to the influx of formation fluid and chemical reactions generated by the plasma in the fluid at the drill bit, the computer 162 can solve the system of equations corresponding to the stoichiometric relationships and to the reaction rate equations between the products and the potential reactants. For known or solvable stoichiometry, reactant concentrations can be calculated directly. For most systems, the stoichiometric equations generate a set of solvable equations with more degrees of freedom than encompassed by product concentration alone. For these systems, estimated reaction rate constants and reaction kinetics can be applied in order to determine reactant concentrations.

Drilling mud for traditional mechanical drilling requires properties that promote mechanical drilling and support pore pressure: i.e. density, viscosity, etc. Drilling mud for pulse power drilling is also an electrical transportation medium, which makes electrical properties, such as dielectric constant, breakdown voltage, resistivity, etc. important qualities. Both electrical and physical properties depend on chemical concentration of the constituent molecules are particulates of the drilling mud which is monitored in traditional mud drilling. Mud logging for pulse power drilling can also include calculation of the stoichiometry and reaction rate of the chemical reactions occurring downhole.

The rate at which a chemical reaction takes place, i.e. the rate at which reactants turn into products, is given by a generalized reaction rate, which depends on a reaction rate constant k(T) and on the concentration of reactants (usually in units of moles per unit volume). The reaction rate constant k can itself be a function of temperature, pressure, and activation energy. The reaction rate for a generalized m+n$^{th}$ order reaction is shown in Equation 22, below, for a rate limiting step involve molecules of species A and B.

$$r=k(T)[A]^m[B]^n \qquad (22)$$

Where r is the reaction rate, k(T) is the reaction rate constant, A and B are reactant molecules and the rate limiting step involves m molecules of reactant A interacting with n molecules of reactant B, such as for a reaction mechanism described by a rate-limiting intermediate step shown in Equation 23 below:

$$m \cdot A + n \cdot B \rightarrow q \cdot P \qquad (23)$$

Where m molecules of A and n molecules of B react to form q molecules of an example product molecule P.

The order of the reaction (zeroth order, first order, etc.) depends upon the reaction mechanisms and the rate limiting step in the reaction and how many and which species of molecules participate in the rarest or slowest collision. The rate limiting step is usually the slowest step of the elementary or intermediate steps that make up the reaction mechanism. For many chemical reactions, the reaction mechanism or the set of intermediate steps that occur when reactants become products has a single step or portion that is observably slower than all other steps. This step functions as a bottleneck or limit on the total reaction speed and is therefore known as the rate limiting step. For a reaction with multiple intermediate steps, the rate limiting step can depend on a catalyst molecule that is not a reactant or a product. For direct current (DC) plasmas with lifetimes in the microsecond (µs) to second range, many hydrocarbon formation reactions depend on intermediate steps involving hydroxyl free radicals, carbonyl free radicals or other free radicals with very short lifetimes, where free radical formation is therefore the rate determining step. Hydroxyl free radical formation and concentration is dependent on water concentration, not hydrocarbon concentration, and upon plasma energy and properties including plasma temperature and geometry. This gives rise to many zeroth and first order reaction rates for generation of alkenes, alkynes, aromatics, and other unsaturated hydrocarbons from alkanes. A zeroth order reaction rate is given by Equation 24:

$$r=k(T)[A]^0=k(T) \qquad (24)$$

where r is the reaction rate, k(T) is the reaction rate constant for a reaction with the rate limiting step that is independent of reactant concentration and where [A] is a reactant concentration. A zeroth order reaction rate does not depend on the concentration of the reactants and has a rate constant with units of moles per second (mol/s) or equivalent. A first order reaction rate depends in the first order (i.e. [A]$^1$) on a reactant and has a rate constant with units s$^{-1}$ or equivalent, as is shown in Equation 25, below.

$$r=k(T)[A] \qquad (25)$$

Where r and k(T) are the reaction rate and reaction rate constant, respectively.

The reaction rate constant k(T) depends on temperature and can be approximated using the Arrhenius equation, as shown in Equation 26 below:

$$k(T)=Ae^{-E_a/RT} \qquad (26)$$

The Arrhenius equation relates the reaction rate constant k to the activation energy $E_a$, the absolute temperature T in Kelvin, the universal gas constant R, and a pre-exponential factor A representing the fraction of molecular collisions resulting in the chemical reaction out of all molecular collisions of the species of the rate limiting step. Alternatively, the Boltzmann constant $k_B$ can be used in place of R if the activation energy $E_a$ is also in units of $k_B T$. An exponential fitting factor β can also be used to correct modeled data to experimental data, as is shown for Equation 27.

$$k(T) = A\mathrm{Exp}\left[-\left(\frac{E_a}{RT}\right)^\beta\right] \qquad (27)$$

Where β is a dimensionless fitting factor used to relate reaction rate constants to observable reaction rates, as a function of temperature.

Formation fluid can be approximated to a first order as containing alkanes, naphthenes (which is a generic name for the family of cycloalkanes), and water. Alkanes, which the general chemical formula $C_nH_{2n+2}$, contain single carbon to carbon bonds (σ bonds) between n sp$^3$ hybridized carbon atoms. Alkanes are saturated hydrocarbons which contain no carbon-carbon double bonds (π bonds) but are rather full hydrogenated—that is the carbon backbone or carbon chain is bonded to the maximum number of hydrogen atoms possible. Naphthenes, which are cyclic alkanes where the carbon chain loops back on itself, have the general chemical formula $C_nH_{2(n+1-r)}$ where n is the number of carbons in the cycloalkane and r is the number of rings in the naphthene molecule. Formation fluid can also contain water, such as salt water, when emanating from water rich rock formations or strata. The generalized chemical equation for the plasma reaction is approximated by Equation 28, below:

$$A_n \cdot C_nH_{2n+2} + B_{n,r} \cdot C_nH_{2(n+1-r)} + D \cdot H_2O \rightarrow E_n \cdot C_nH_{2n+2} + \\ F_{n,r} \cdot C_nH_{2(n+1-r)} + G_n \cdot C_nH_{2n} + I_n \cdot C_nH_{2n-2} + J \cdot CO_2 + \\ K \cdot O_2 + L \cdot H_2 \qquad (28)$$

where $A_n$ is the stoichiometric coefficient for a reactant alkane of n carbon atoms with the molecular formula $C_nH_{2+2}$, $B_{n,r}$ is the stoichiometric coefficient for a n carbon naphthene reactant molecule with r rings with the molecular formula $C_nH_{2(n+1-r)}$, $E_n$ is the stoichiometric coefficient for a product alkane of n carbon atoms with the molecular formula $C_nH_{2n+2}$, $F_{n,r}$ is the stoichiometric coefficient for a n carbon naphthene product molecule with r rings with the molecular formula $C_nH_{2(n+1-r)}$, $G_n$ is the stoichiometric coefficient for an n carbon alkene with molecular formula $C_nH_{2n}$, and $I_n$ is the stoichiometric coefficient for an n carbon alkyne with molecular formula $C_nH_{2n-2}$. D is the stoichiometric coefficient for water ($H_2O$), J is the stoichiometric coefficient for carbon dioxide ($CO_2$), K is the stoichiometric coefficient for oxygen ($O_2$), and L is the stoichiometric coefficient for hydrogen ($H_2$).

The stoichiometric coefficients for each of the hydrocarbon species (i.e. $A_n$, $B_{n,r}$, $E_n$, $F_{n,r}$, $G_n$ and $I_n$) depend both on the number of carbons of the type of hydrocarbon (i.e. n) and the isomer (or atomic arrangement) of those carbons, but can be approximated as independent of isomeric configuration in order to simplify measurements. Table 1, below, contains names and formulas alkanes, alkenes, and alkynes as a function of the number of carbons they contain. As the molecules become larger (i.e. as n increases) the number of isomer molecules for each chemical formula increase, where isomers are various physical arrangements and chemical bonds possible for the same atoms. For n>2, polyunsaturated hydrocarbons also occur (i.e. hydrocarbons with two or more double bonds). Unsaturated hydrocarbons such as alkanes, are carbon molecules that contain only hydrogen and carbon and have the maximum number of hydrogen constituents possible for the given amount of carbon atoms. The ability to detect or differentiate hydrocarbons, including isomers, from one another depends on the specificity of instrumentation and is non-trivial.

As the number of carbons grows, the number of isomers increases—eventually increasing exponentially. For a hydrocarbon consisting of 40 carbon atoms and 82 hydrogen atoms, there are larger than 62 million isomers. Decane, $C_{10}H_{22}$, has 75 isomers. In some embodiments, hydrocarbons with large numbers of isomers are grouped by carbon atom amount instead of determined or quantified by individual isomer. Alkenes and alkynes have more isomers than alkanes because the location of the double or triple bond contributes to isomer multiplicity. In some embodiments, the number of isomers considered large is over ten. In other embodiments, hydrocarbon molecules with ten or more carbon atoms can be considered to have large numbers of isomers. Hydrocarbons can be grouped by those with large numbers of isomers, which can be measured as a function of carbon count and not individually resolved, or can be grouped into isomeric groups that can be resolved by molecular weight or gas chromatography or another separation analysis.

The stoichiometry balance of the reaction can be determined based on the measured composition of the drilling fluid. The drilling fluid is measured as it exits the wellbore—hydrocarbon concentrations are measured as are types and volumes of evolved gasses. The composition of the drilling mud pumped downhole is either measured as circulates back downhole, or the measured composition of the drilling mud returned to the surface is set as the drilling mud concentration when that mud recirculates into the wellbore. In either case, an initial drilling mud concentration is subtracted from a final drilling mud concentration, which generates the change in concentration for various species occurring downhole.

Figure 4A:
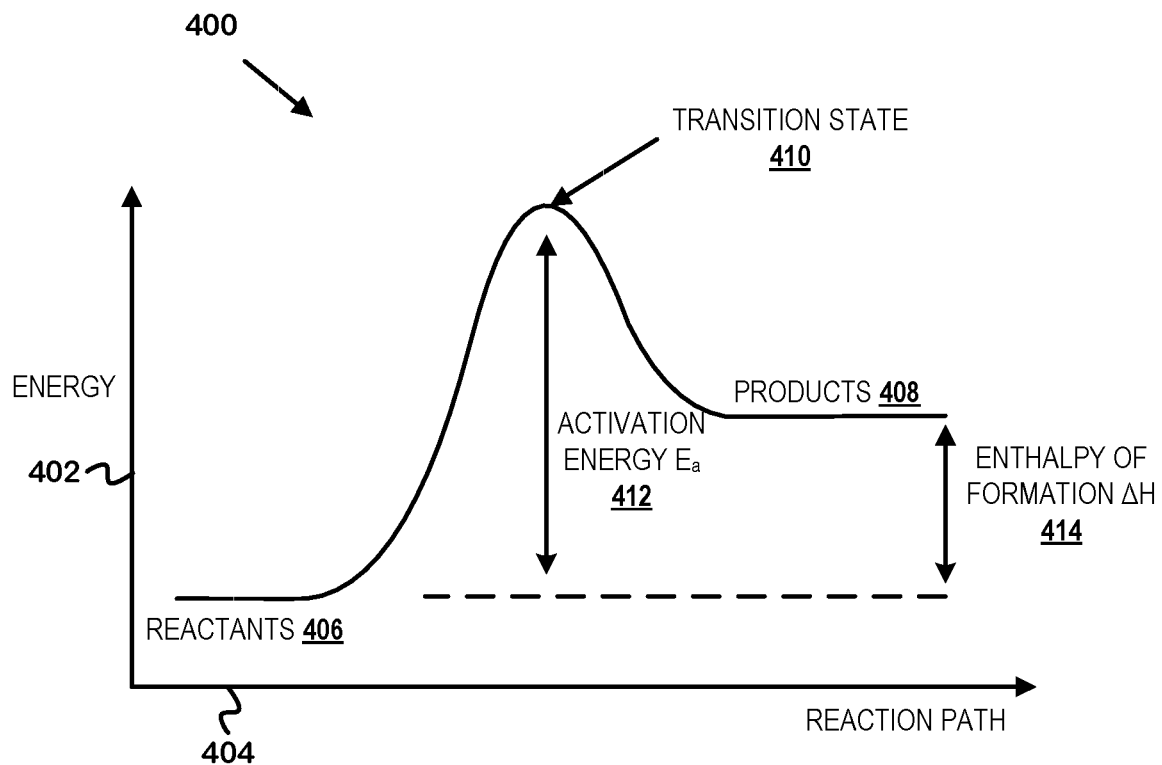
FIG. 4A depicts an example line graph of the reaction kinetics and reaction path of an example plasma-mediated chemical reaction, according to one or more embodiments.

To help illustrate, FIG. 4A depicts an example line graph of the reaction kinetics and reaction path of an example plasma-mediated chemical reaction, according to some embodiments. In particular, FIG. 4A depicts a graph 400 having a y-axis for energy 402 and an x-axis for a reaction pathway 404. The graph 400 depicts example reaction kinetics and molecular energies for example reactants and products of a pulse plasma. The plasma energy, which is the energy added to the system consumed to generate the plasma, can create highly energized particles, both kinetically energized and energized electronically above the ground state. Energized molecules and atoms therefore interact more frequently and can form transition states favorable to reaction. The graph 400 depicts an example reaction pathway (also known as a reaction path) for a set of reactants, their intermediate transition state, and the final products of the example reaction. Activation energy $E_a$ 412 is the energy per set of reactants or per reaction needed to reach transition state 410, where the transition state 410 is a complex formed between the atoms of the reactant molecules that is the highest energy state during the chemical transformation from the reactant species to the product species.

For most of the hydrocarbon reactions occurring in the plasma, reaction products 408 will have a greater enthalpy of formation 414 than reactants 406 (i.e. higher energy 402). Enthalpy of formation is a measure of the energy contained within a molecule as a sum of the energies contained within the chemical bonds between the constituent atoms. The plasma energy can be defined as the total energy in the plasma. The plasma energy added to the fluid is stored in higher order carbon bonds. Each molecular reaction can store the enthalpy of formation 414 (as an amount of energy)

TABLE 1

Common Hydrocarbons

| N | Formula | Alkane | Isomers | Formula | Alkene | Isomers | Formula | Alkyne | Isomer |
|---|---|---|---|---|---|---|---|---|---|
| 1 | $CH_4$ | Methane | 1 | | | | | | |
| 2 | $CH_3CH_3$ | Ethane | 1 | $CH_2=CH_2$ | Ethene | 1 | $HC\equiv CH$ | Acetylene | 1 |
| 3 | $CH_3CH_2CH_3$ | Propane | 1 | $CH_3CH=CH_2$ | Propene | 1 | $HC\equiv CCH_3$ | Propyne | 1 |
| 4 | $CH_3(CH_2)_2CH_3$ | Butane | 2 | $CH_3CH_2CH=CH_2$ | Butene | 4 | $CH_3C\equiv CCH_3$ | Butyne | 2 |
| ... | | | | | | | | | |
| 40 | $C_{40}H_{82}$ | | Large | $C_{40}H_{80}$ | | Large | $C_{40}H_{78}$ | | Large |

In general, the products of the chemical reaction of Equation 28 have higher enthalpy or energy of formation that the reactants, which will be described in more detail below in reference to FIGS. 5A-5B. This higher energy corresponds to the energy balance, where the energy added to the plasma is stored in higher order chemical bonds and endothermic reactions are favored by high energy transition states.

within the reaction products' 408 chemical bonds. The reaction energies include the activation energy $E_a$ 412 and the enthalpy of formation 414, and can be defined as the energy needed for a set of reactants 406 to reach the transition state 410 or stored in the reaction products 408. The reaction energy can be measured on a per reaction or molar basis. When species collide and react, the frequency at which the transition state 410 arrangement of the hydrocarbon is reached is a function of the kinetic energy added to the molecule through absorption of a photon, stabilized via hydroxyl, or other catalysis processes. In a plasma, the kinetic energy of the particles is high because the plasma energy is high. The plasma energy is a measure of the kinetic energy of the particles and molecules within the plasma, and higher energy transition states are allowed (and occur more frequently), as shown along the reaction pathway 404.

In the graph 400, the reaction pathway 404 is a simplified timeline of the reaction, going from the reactants 406 to the reaction products 408 (showing an intermediate step—the transition state 410). Reaction mechanisms, which include possible reaction pathways and intermediate steps, can be much more complicated. A reaction mechanism can be defined as the series of steps and chemical rearrangements that occur during a reaction at a molecular level, where reactants transform into products. A reaction mechanism may include intermediate steps, some of which can lead to formation of multiple different reaction products. A reaction path or reaction pathway can be defined as the method or steps of the reaction mechanism which lead from a set of reactants to a set of reaction products. A reaction can have more than one pathway that generates identical reaction products from reactants (as will be discussed in reference to FIG. 4B), and each pathway can have a different activation energy and reaction rate. For instance, catalysts can stabilize transition states thereby lowering activation energies and increasing the speed of a given reaction rate, but even in catalyzed reactions a portion of the products may be generated through the higher energy uncatalyzed transition state. Reactions, including intermediate reaction steps, can also be reversible which means that a significant portion of the reaction products re-react to re-from the reactant species. Dehydrogenation reactions tend to be irreversible because the gaseous reaction products quickly dissociate from the hydrocarbon species, but transition states in dehydrogenation reactions are likely to form reaction products or to re-form reactants.

Plasma energy (of the entire plasma) and reaction energy (of each individual chemical reaction) can be correlated—higher plasma energy favors reactions with larger activation energies and greater enthalpy of formation. The concentration of product species multiplied by the enthalpy of formation of each species generates a total reaction energy for the chemical reactions within the plasma that can be compared to the plasma energy.

Figure 4B:
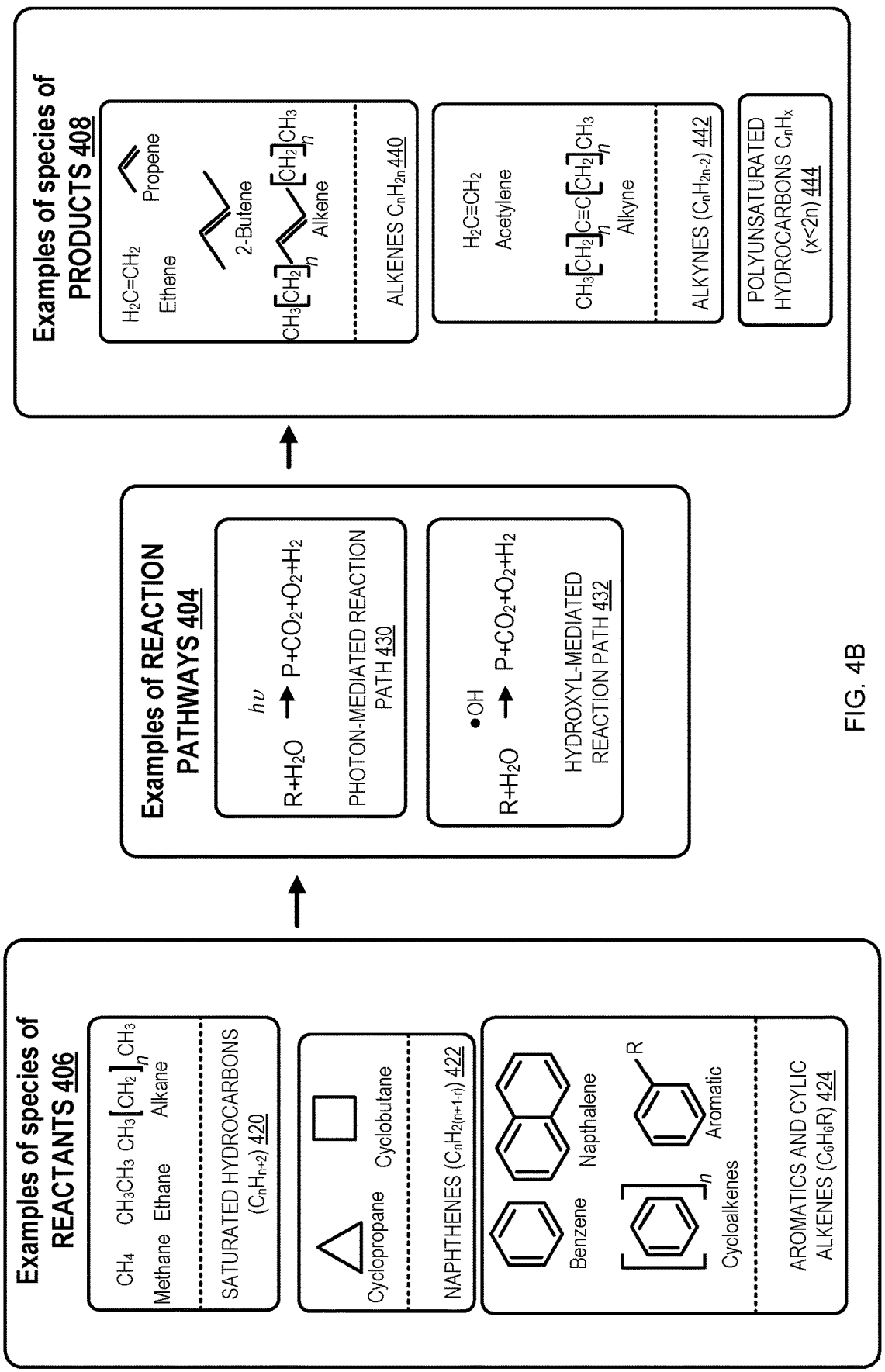
FIG. 4B depicts example reactants and products as well as example reaction pathways, according to one or more embodiments.

To further illustrate, FIG. 4B depicts example reactants and products as well as example reaction pathways, according to some embodiments. FIG. 4B depicts examples of species of reactants 406, examples of reaction pathways 404, and examples of species of reaction products 408. In order to calculate the formation fluid concentration, a set of equations based on reaction rate constant and final or product concentration can be generated. For a generic product molecule, P, of the first order reaction shown in Equations 29 and 30, the final concentration [P] can be known and measured at the surface during drilling mud analysis.

$$R \rightarrow P \tag{29}$$

$$r = k(T)[R] = -\frac{d[R]}{dt} = \frac{d[P]}{dt} \tag{30}$$

Where R is a generic reactant and P is a generic product of the first order reaction of Equation 29. [R] is a concentration of molecule R, [P] is a concentration of molecule [P], r is a reaction rate, and k is a reaction rate constant which is a function of temperature T.

Product species P can include at least one species from at least one of alkenes 440, alkynes 442, polyunsaturated hydrocarbons 444, and any of those species included corresponding to reactant species R. Reactant species R can include species from at least one of the alkanes or saturated hydrocarbons 420, the naphthenes 422, or the aromatics and cyclic alkenes 424, as can be found in the formation fluid. If the reaction rate constant k(T) is also known, the reactant concentration [R] (which is the formation fluid concentration) for a generic product P is directly calculable according to Equation 31-33 below:

$$[P] = r * \Delta t = k(T)[R] * \Delta t \tag{31}$$

$$[P] = \int r dt = \int k(T)[R] dt \tag{32}$$

$$[R] = \frac{[P]}{k(T) * \Delta t} \tag{33}$$

where the concentrations of P and R change as the reaction occurs. Concentration changes may be large enough that the change in reactant concentrations favors the use of integrals (as shown in Equation 32) instead of discrete analysis (as shown in Equations 31 and 33). The instantaneous product concentrations may not be known, as can occur when drilling mud circulation prevents instantaneous measurement of chemical reaction products. If the instantaneous concentrations are not known, the reaction rate and reactant concentration can be approximated using integral approximation, such as for an exponential concentration approximation, or discrete analysis.

A product molecule(s) P can be generated from a reactant molecule(s) R via an example photon-mediated reaction pathway 430 or an example hydroxyl-mediated pathway 432. The ratio between reactions catalyzed by light and those catalyzed by hydroxyl free radicals can correspond roughly to the ratio between plasma arc and plasma spark.

For the set of alkane dehydrogenation reactions (which can be considered to be the opposite of cracking reactions) encompassed by Equation 28 (set forth above), the molar concentrations of hydrogen, carbon dioxide, and oxygen gases can be determined at the surface. From the oxygen mass balance of the chemical reaction, the relationship between coefficients D, J, and K is determined, as shown in Equation 34.

$$D=2(J+K) \tag{34}$$

Where D is the stoichiometric coefficient for water, J is the stoichiometric coefficient for carbon dioxide, and K is the stoichiometric coefficient for hydrogen as defined in the chemical reaction of Equation 28. This allows the initial concentration of water to be calculated based on the measured molar concentrations of carbon dioxide and oxygen measured at the surface, as is shown in Equation 35, below:

$$[H_2O]=2([CO_2]+[O_2]) \tag{35}$$

The mass balance of the carbon and hydrogen atoms can be complicated by the multiplicity of the hydrocarbon species. The chemical analysis does not necessarily determine a concentration for each isomer of the saturated and unsaturated hydrocarbons. Isomer concentrations, where available, can refine available mass balance equations. The chemical analysis equipment can identify concentrations of hydrocarbons as a function of n and carbon to hydrogen (C/H) ratio with great specificity. The total carbon balance is given by Equation 36 and the total hydrogen balance is given by Equation 37.

$$\sum_{i=1}^{n} i*A_i + \sum_{i=1}^{n}\sum_{j=1}^{r} i*B_{i,j} = \sum_{i=1}^{n} i*E_i + \sum_{i=1}^{n}\sum_{j=1}^{r} i*F_{n,j} + \sum_{i=1}^{n} i*G_i + \sum_{i=1}^{n} i*I_i \quad (36)$$

$$\sum_{i=1}^{n} 2(i+)*A_i + \sum_{i=1}^{n}\sum_{j=1}^{r} 2(i+1-j)*B_{i,j} + 2D = \sum_{i=1}^{n} 2(i+1)*E_i + \sum_{i=1}^{n}\sum_{j=1}^{r} 2(i+1-j)*F_{n,j} + \sum_{i=1}^{n} 2i*G_i + \sum_{i=1}^{n} 2(i-1)*I_i + 2L \quad (37)$$

Again, the stoichiometric coefficients for each of the hydrocarbon species (i.e. $A_n$, $B_{n,r}$, $E_n$, $F_{n,r}$, $G_n$ and $I_n$) come from Equation 28 previously and represent the total equation mass balance for each of the carbon species with n carbons.

The stoichiometric coefficients for the hydrocarbon species—$A_n$, $B_{n,r}$, $E_n$, $F_{n,r}$, $G_n$ and $I_n$—appear in both the carbon mass balance and the hydrogen mass balance (which also includes coefficients D and L). The stoichiometric coefficient D, J, and K are related based on the oxygen balance previously discussed in relation to Equations 34 and 35. The stoichiometric coefficients are constrained by these equations, which becomes a solvable system of equations for coefficients of the reaction.

The final concentrations of species can also be known, where $[CO_2]$, $[O_2]$, $[H_2]$ can be measured directly. If not all water is consumed during the plasma-driven chemical reaction, the initial concentration of water can be calculated directly from the gaseous product concentration and the final concentration of water in the drilling fluid, given by Equation 38:

$$[H_2O]_{initial} = [H_2O]_{final} + 2([CO_2]_{final} + [O_2]_{final}) \quad (38)$$

where initial denotes the concentration in the formation fluid and drilling mud downhole before the plasma reaction, and final denotes the concentrations measured in the drilling fluid after the reaction (either at the surface or with analysis equipment downhole). If the drilling mud contains water when it is pumped downhole, the formation fluid's water concentration can then be given by Equation 39, which accounts for a change in water concentration due to formation fluid influx.

$$[H_2O]_{initial} = \Delta[H_2O]_{drilling\ fluid} + 2([CO_2]_{final} + [O_2]_{final}) \quad (39)$$

Where the change in drilling concentration in the drilling fluid is represented by $\Delta$, which is the change in the water concentration measured in the drilling fluid before and after the reaction.

Product hydrocarbon concentration $[C_nH_{2n+2}]$, $[C_nH_{2(n+1-r)}]$, $[C_nH_{2n}]$, and $[C_nH_{2n-2}]$ can also be calculated or determined, based on direct measurement or inference. For example, with reference to FIG. 1, the computer 162 can perform this operation. The known and unknowns together create a system of equations where the initial formation concentrations are solvable. Further, reaction kinetics allow refining of the concentrations based on known product concentration and calculable reaction rates, as shown in Equations 24-25 (set forth above).

If reaction rates are known (i.e. can be calculated based on product concentrations as a function of time) and the reaction order of the rate limiting step (i.e. first order, second order, etc.) is known, then exact concentrations of reactants are calculable from product concentrations. For hydrocarbon dehydrogenation, most reaction rates are first order or zeroth order. Zeroth order reactions depend on time, not on reactant concentration (to a first approximation). Product concentrations follow Equation 40.

$$[P] = k(T)*\Delta t \quad (40)$$

Where [P] is the concentration of a generic product molecule P and $\Delta t$ is the lifetime of the reaction. These types of reaction kinetics correspond to chemical reactions dependent on free radicals, equilibrium rearrangement at high temperature (such as for hydrocarbon isomers in equilibrium), and for catalyzed reactions where k may be zeroth order with respect to reactants but depend on the concentration of a catalyst. For first order reactions, product concentrations can be related to reactant concentrations as shown in Equation 41.

$$[P] = k(T)[R]*\Delta t \quad (41)$$

Where [R] is the concentration of a generic reactant molecule R. Where the concentration of R is also a function of time, this equation becomes Equation 42:

$$[P] = \int k(T)[R]dt \quad (42)$$

In general, the concentration of a first order reactant as a function of time is given by solving the rate equation to get Equation 43, below:

$$[R] = [R]_0 e^{-k(T)*t} \quad (43)$$

Where $[R]_0$ is the initial concentration of generic reactant R, k(T) is the reaction rate constant, and t is time. Substituting Equation 43 into Equation 42 yields equation 44:

$$[P] = \int k(T)[R]_0 e^{-k(T)*t} dt = k(T)[R]_0 \int e^{-k(T)*t} dt = [R]_0 e^{k(T)*t} \quad (44)$$

Where this relationship holds when one molecule of reactant R yields one molecule of product P. The product concentration for first order reactions can be similarly related to reactant concentrations for different stoichiometric relationships as well.

By correlating reaction rate constant to temperature and plasma power, rate constant values are further refined. The rate constant for a plasma reaction can be a function of temperature, plasma power, and activation energy. Activation energy for transition states are known. Determination of a reaction rate constant for a first order reaction can be made by varying the plasma power (where temperature is constant, and activation energy is a function of the transition state and therefore constant for the specific reaction mechanism). This is shown in Equations 45-47, below, where the reactant concentration [R] is a function of the formation and does not vary over the time scale of the power analysis.

$$[P]_1 = k(T, PW_1)[R]*\Delta t = [R]_0 e^{k(T,PW_1)*t} \quad (45)$$

$$[P]_2 = k(T, PW_2)[R]*\Delta t = [R]_0 e^{k(T,PW_2)*t} \quad (46)$$

$$\frac{[P]_1}{[P]_2} = \text{Exp}[k, (T, PW_1) - k(T, PW_2)] = f\left(\text{Exp}\left(\frac{PW_1}{PW_2}\right)\right) \sim f(PW) \quad (47)$$

Where P represents the product concentration and PW represents the plasma power. PW is used so that power is not confused with either product concentration [P] or pressure as used previously. Subscripts 1 and 2 denote a first power setting and its corresponding concentrations, temperature, and time, and a second power setting and its corresponding concentrations, temperature, and time. T is temperature and t represents time. The power analysis can be simplified if all time and temperatures remain constant while power is varied, so that the relationship between k(T) and power can be explored.

The dependence of the rate constant on plasma power can be determined from the product concentrations as a function of power. Once the relationship between rate constant k and plasma power is known, then the relationships between reactant concentration and product concentration can generate another set of equations that further restrict the degrees of freedom of the system.

The reaction rate constants can also vary by plasma type. For example, the reaction rate constants for plasma arcs can be different than the reaction rate constants for plasma sparks even for similar products and reactants over the same rate limiting step. Certain reaction products are favored by different types of plasma, as previously discussed in relation to hydroxyl free radical formation and hydroxyl-mediated versus photon-mediated reaction pathways. Reaction rate constants for each type of plasma can be determined via at least one of a plasma power analysis or a spark versus arc ratio analysis.

The relationship between the product and reactant concentrations can thereby be constrained enough to allow for solving for reactant concentrations based on measured product concentrations and plasma parameters. These solutions can be determined directly, with sufficient product information, or can be solved iteratively or by machine learning applied to a body of data.

Returning to operations of FIG. 3 at block 319, the fluid loss or influx is estimated based on the concentration of species in the drilling mud. Influx of formation fluid into the wellbore or loss of drilling mud to the formation can be further determined based on the ratio of plasma reaction products. For example, with reference to FIG. 1, the computer 162 can perform this estimation. The computer 162 can determine a ratio between hydrogen and small molecular weight hydrocarbons or between hydrogen and aromatics or between small molecule alkanes and aromatics in order to estimate the amount of drilling fluid lost to the formation or the fluid volume gained due to an influx of formation fluids. The computer 162 can also estimate the total volume of drilling fluid returned to the surface using instrumentation 161 or fluid reconditioning system 142.

Drilling fluid or mud is necessary to maintain pressure downhole above the pore pressure of the formation. If the pressure downhole is below the pore pressure of the formation, the pressure downhole can be considered too low as gas and fluid can enter the wellbore from the surrounding formation. For reactive gases like $H_2$ and $H_2S$, entrance of dissolved gasses into the drilling mud can lead to corrosion downhole and can lead to violent or explosive evolution as the drilling mud moves towards lower pressures at the surface. If the pressure downhole is above the formation fraction pressure, the pressure downhole can be considered too high as the wellbore or wellbore walls may collapse as the formation is fractured or destroyed by drilling mud forces into weaker strata. Monitoring the amount or volume of drilling mud returned to the surface allows mud logging to estimate the influx of fluid into the wellbore or the loss of fluid to the formation. Pulse power drilling can complicate this determination because the chemical reactions downhole generate gaseous products, in addition to vaporization of water (from aqueous fluids) and carbon dioxide and the like dissolved in hydrocarbon fluids. Many of the gasses generated downhole via the plasma will dissolve, under pressure, back into the drilling fluid (which can be assumed to be a non-Newtonian high temperature and high-pressure fluid) as the plasma is quenched. The gaseous products are detectable via low pressure or low temperature gas extraction, or distillation, from the drilling fluids.

Further, influx and loss can be detected by a shift in the chemical composition of the drilling fluid, or product concentrations in the drilling fluid. When drilling fluid is lost to the formation, that loss can result in a steadier drilling fluid chemical composition. The drilling fluid returned to the surface can significantly match the composition of the drilling fluid that was pumped downhole. The loss to the formation limits the amount of hydroxyl free radicals created from water molecules available to catalyze the chemical reactions downhole, and therefore slows reaction rates.

In the case of an influx into the wellbore, formation fluid and product concentration in the drilling fluid can increase. Saltwater flow into the wellbore can significantly increase the amount of hydrogen gas detected at the surface. The ions present in the saltwater increase the fractional ionization of the plasma formed downhole. The increase in hydroxyl groups (where water readily decomposes into hydroxyl groups and hydrogen) can increase reaction rates, but significantly increases the production of hydrogen molecules at a rate greater than the increase for other products. An influx of gas from the formation increases the concentration of methane and short carbon products. Hydrocarbon gas is already heavy in small molecular weight carbon species (i.e. approximately $n \le 10$), and these reactants tend to crack and form small unsaturated molecules or merge but remain small in the presence of catalyst. An influx of oil from the formation, where oils contain high molecular weight hydrocarbons, can lead to an increase in the complex, aromatic, and unsaturated product species and concentrations.

The total volume of drilling fluid or drilling fluid level in the mud pit remains a valuable method of measuring formation loss and influx. However, monitoring the products of the chemical reactions downhole enable mud logging to further record information about the formation fluid.

At block 320, the determined formation fluid concentrations are refined by correlating reaction rates to plasma energy. Reaction rate calculations can be applied in order to generate additional equations to better define the system of linear equations to generate a definite solution. For example, with reference to FIG. 1, the computer 162 can perform this operation. Many of the reaction pathways can share transition states, where transition states determine the activation energy $E_a$ of a reaction pathway. For reactions with known activation energy, the reaction rate constant can be calculated directly from the measured temperature at the plasma (based on the Arrhenius or similar equation) or can be estimated based on a plasma power analysis performed in the wellbore previously.

Free radicals are high energy and unstable, especially in alkanes. The hydroxyl radical has the longest lifetime of the free radicals produced downhole. The chemical reactions occur at equilibrium in the plasma, where high velocity electrons enable formation of transition states. For photon-emitting plasmas, photons can generate excited states inside the plasma and in surrounding fluid. Without regard to which excitation mechanism generates the transition state, products are generated as the plasma is quenched and further chemical transitions become energetically unfavorable.

Further information is gained via periodic off bottom plasma generation events. The drilling bit is retracted from the wellbore bottom and suspending in the wellbore surrounded by drilling fluid (or only partially introduced into the well) and a plasma is generated, the contribution of the drilling fluid to the reaction rate and product species is then measured. The drilling fluid plasma products is then subtracted from the total product concentration measured at the surface, in order to selectively identify the reaction products corresponding to the formation and formation fluid at the wellbore bottom. The off bottom analysis can also be conducted for a variety of plasma powers, in order to determine the arc vs. spark ratio of each plasma power setting which can be extrapolated as the arc vs. spark ratio for the wellbore bottom plasma in the formation.

At block 322, a relation between the plasma arc and the plasma spark is calculated based on concentrations, gas species, and volume of the drilling mud. For example, a ratio between the plasma power that generates the plasma arc and the plasma power that generates any plasma sparks can be calculated. For example, with reference to FIG. 1, the computer 162 can make this calculation. This relation may be calculated as a ratio, a fraction, a percentage, or a range. The relation between the arc and spark for the plasma can depend on the power used to generate the plasma and upon wellbore geometry and dielectric characteristics. As discussed in reference to FIGS. 2A-2C (and further discussed in reference to FIGS. 4A-4B and 5A-5B below), both porosity and permeability along with formation fluid resistivity, can contribute both to the total dielectric strength between the anode and cathode and to the distribution of plasma arcing vs. sparking. Plasma arcs and plasma sparks can produce distinctive products and the relation of these products can correspond to the relation between the plasma arc and spark. For instance, plasma sparks generate high temperature, more spherical plasma, and vapor bubbles in fluid. Whereas, plasma arcs generate lower temperature, more elongated bubbles with longer lifetimes. Certain species, for example, are preferentially formed in each type of plasma. For example, plasma sparks favor formation of hydroxyl catalyzed reaction and produce a significant amount of hydrogen. Whereas, plasma arcs favor photon catalyzed reactions, where ultraviolet (UV) photons especially promote carbon-carbon bond formation especially cyclic alkanes (naphthenes).

Figure 5A:
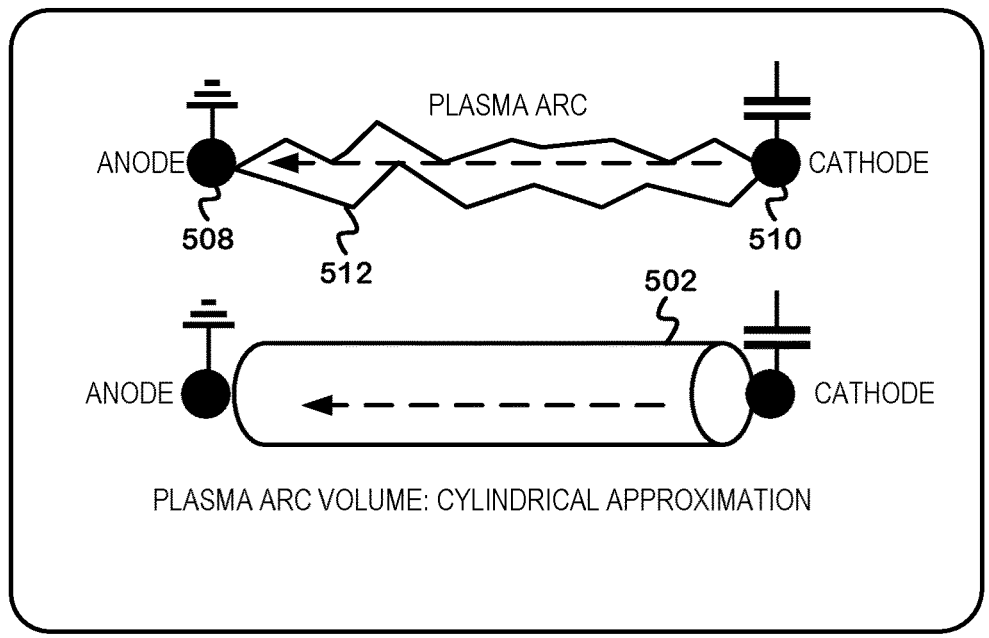
FIG. 5A depicts the geometric approximation for a plasma arc, according to one or more embodiments.
Figure 5B:
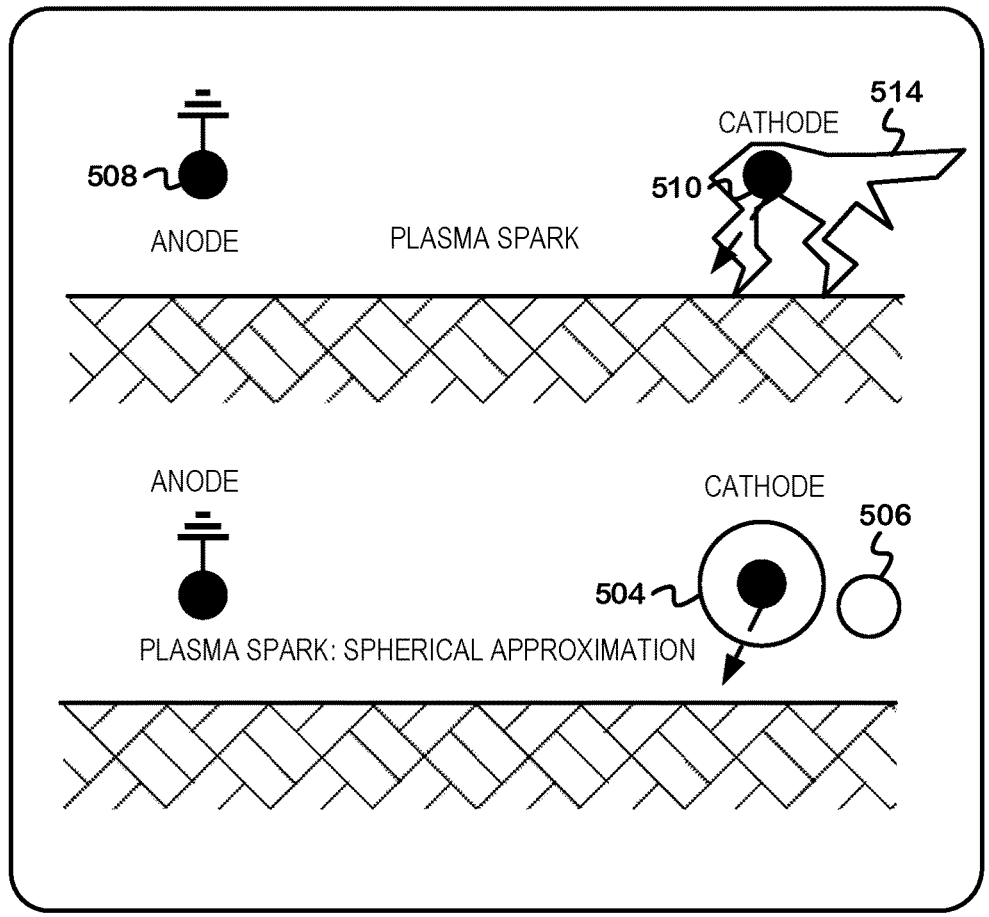
FIG. 5B depicts the geometric approximation for a plasma spark, according to one or more embodiments.

To help illustrate, FIGS. 5A-5B depict example geometric approximations for a plasm arc and a plasma spark, respectively. FIG. 5A depicts the geometric approximation for a plasma arc, according to one or more embodiments. FIG. 5A depicts a plasma arc 512 between an anode 508 and a cathode 510. The plasma arc 512 can be generated as DC plasma discharges, between the anode 508 and the cathode 510. As shown, the plasma arc 512 appears as jagged emissive paths as the DC plasma discharges. AC plasma discharges tend to have a softer more even glow and are usually contained by a magnetic field. The plasma arc 512 is visible because highly energetic electrons and molecules are created, which emit photons as they decay back to their ground states.

Within a plasma, particles can be so energetic that chemical bonds are in flux. The chemical composition of ions and molecules can be set when they leave the plasma, either because the plasma is quenched, or because their kinetic energy takes them outside of the plasma bounds. In either case, the chemical reactions can occur at the boundaries of the plasma where each species no longer experiences the excitation or collisions for it to reach a transitional state (as explained in reference to FIGS. 4A-4B above). The chemical reaction rates for formation of complex hydrocarbons from alkanes and naphthenes (as described in Equation 28) can depend most closely on the concentration of hydroxyl radicals and on energetic photons, both of which function as catalysts for such reactions. As depicted in FIG. 5A, the plasma arc 512 can be approximated as a cylinder 502 sustained by electrons from the anode 508 to the cathode 510 and generate larger, elongated gas-phase bubbles.

FIG. 5B depicts the geometric approximation for a plasma spark, according to one or more embodiments. FIG. 5B depicts a plasma spark 514 between the anode 508 and the cathode 510. The plasma spark 514 can be generated as a DC plasma discharges between the anode 508 and the cathode 510. As shown, the plasma spark 514 appears as a jagged branching path surrounding the cathode 510. The plasma spark 514 can represent the plasma generated that does not complete the circuit between the anode 508 and the cathode 510. Plasma spark 514 is visible because, as for the plasma arc, highly energetic electrons and molecules are created, which emit photons as they decay back to their ground states. The plasma spark 514 tends to generate spherical bubbles 504, 506 as a result of hydrodynamics.

Each type of plasma also trends towards a different plasma temperature. Plasma arcs have lower electron temperatures than plasma sparks, where plasma sparks have higher electron kinetic energy because more energy is required to create a plasma in the absence of the strong electric field between the anode and cathode. The individual reactions occurring in each type of plasma can be the same, but the dominant reaction mechanisms can differ as a result of differences in surface area and temperature.

Returning to FIG. 3 at block 326, the plasma energy and reaction rate estimates and calculations are updated based on the arc to spark ratio. For example, with reference to FIG. 1, the computer 162 can perform this update. The arc to spark ratio can be estimated and updated, along with the other reaction and plasma parameters, until the stoichiometric equations balance and concentrations of formation fluid species are determined. The computer 162 can determine the reactant concentrations exactly or to within a preselected error range. Such a determination can involve an iteration of all factors, multiple iterations, look up of reaction rate constants based on plasma power, or based on machine learning. The computer 162 can maintain a record of the drilling mud species concentration before and after the plasma is applied (i.e. before the mud is pumped downhole and then at the surface) in order to correctly account for species in the drilling fluid, species in the formation fluid, and the species that are reactants in the plasma chemical reaction (measured as chemical products).

At block 328, the electrical properties of the formation at the drill bit are determined. For example, with reference to FIG. 1, the computer 162 can make this determination based on the determination of the formation fluid (found in the pore spaces), the arc versus spark ratio, and the plasma power lost to the formation. The electrical properties of the dielectric, including breakdown voltage and resistivity, can correlate to fluid and rock properties.

At block 330, the formation permeability is determined based on the porosity determined at block 312 and the electrical characteristics of the formation fluid and formation calculated at block 328. For example, with reference to FIG. 1, the computer 162 can make this determination. The permeability can be defined in terms of the interconnectedness of the pore spaces, or pore throat size or pore diameter, and in relation to the pore volume.

Permeability is a measure of the formation's or formation strata's ability pore connectivity or ability to transmit fluids and is an important petrophysical property. The permeability of a formation effects the dielectric constant of the combined drilling mud, formation fluid, and rock. The permeability of the formation correlates to the arc to spark ratio, where interconnected pores (which are more permeable) are also more conductive. High permeability formation layers can bias arc formation, where the connection between the anode and cathode and current transport between them happens preferentially in the pore spaces. Interconnected pores can provide a conductive (or more conductive) path for electrons, over which the breakdown voltage will be reached more quickly and where the plasma will form. Low permeability rocks, where pores are not connected or with smaller pores, will preferentially form sparks where there is no free electron path between the anode and cathode. Charge carriers in fluids are intrinsically more mobile than charge carriers in solids, especially ionic solids and insulators.

The combination of porosity and permeability determination allow rock formation type determination. Formation layer type can be determined based on lithology related to formational fluid, rock porosity, and permeability or can be determined based on the characterized formation information based on machine learning or discrete analysis.

At block 332, the formation and formation fluid are determined as a function of depth. For example, with reference to FIG. 1, the computer 162 can determine the types of formation and formation fluid type based on one or more of porosity, permeability, electrical characteristics, and formation fluid composition. The computer 162 can also correlate plasma and chemical parameters to formation layers identified at the depth of the drill bit. The computer 162 can output a mud log analogous to those obtained for traditional mechanical drilling, or can additionally output plasma parameters and major product species as a function of depth.

B. Example Operations for Subsurface Rock Formation Evaluation Based on Plasma Chemistry During pulse power drilling, the exposed structure of the subterranean formation can interact with the generated plasma and impact the chemical reactions downhole. The formation may act as either a catalyst or an inhibitor to either enhance or reduce the rate of chemical reactions as a function of the exposed structure. The exposed structure can function as a reaction surface or matrix, as nucleation sites, etc., for the dehydrogenation reactions of Equation 28 or for other chemical reactions, where reaction enablement is based on porosity, surface roughness, atomic composition of surface sites, etc. The generated plasma can interact with the solid material of the formation, as depicted in FIGS. 2A-2C, where such an interaction can cause a shift in the chemical reactions that can be correlated to the formation (i.e. formation type, porosity, etc.). The generated plasma can also volatize, vaporize, or liquify portions of the formation material, such as water-rich clay matrices, carbonate rocks, silica formations, etc. As the formation is broken up, particles or vapors containing formation ions, atoms, or molecules can become part of the plasma reaction and participate as reactants in the chemical reactions downhole. Accordingly, various attributes of the formation (e.g., type of formation) can be determined by analyzing the shifts in the plasma reactions and the products of the plasma reactions due to influence of the formation.

FIG. 6 depicts a flowchart of example operations for determining rock type based on plasma chemistry, according to one or more embodiments. Embodiments of the example operations described and illustrated in a flowchart 600 of FIG. 6 may include operations that are performed by a pulse power drilling system 100, as illustrated and described with respect to FIG. 1 above. However, program code naming, organization, and deployment can vary due to arbitrary programmer choice, programming language(s), platform, etc. Operations of the flowchart 600 begin at block 602.

At block 602, pulse power drilling mud logging is performed. The pulse power drilling mud logging can be performed as depicted in flowcharts 300-350 of FIGS. 3A-3B or can be performed in an alternate manner. The pulse power drilling mud logging can measure formation fluid as a function of time, which is related to drilling depth in the wellbore via the circulating drilling mud, and provides information about the chemical composition of drilling fluid which has interacted with an electric pulse emitted from the drill bit of the drill string.

A power analysis can be performed to determine the amount or type of rock interacting with the plasma. The amount of formation vaporized or crushed can correlate to the amount of power supplied to the formation and the electrical characteristics of both the plasma and the formation. As the power supplied to the generate the plasma increases, the amount of formation material vaporized can expected to increase which can correlate to an increase in the exposed surface area of the formation or cuttings interacting with the plasma. Higher power pushes the reactions to more complete products, such as hydrogen, carbon dioxide, and oxygen. Higher power may also increase halogen production, if halogens are present. As described above, the amount of rock interacting with the plasma can also be determined. Further, an arc to spark ratio can be correlated to physical or electrical properties of the formation. Higher power may equate to more arc than spark. For example, the arc to spark ratio can provide information about the formation such as breakdown voltage, conductivity, resistivity, Young's modulus, shear modulus, bulk modulus, Poisson's ratio, anisotropy, etc., especially if correlated to drilling rate. Plasma arc and plasma sparks generate different types of fluid bubbles in the formation and consequently interact differently with the formation, particularly if the formation is anisotropic. Further, the chemical reactions mediated by plasma arc and plasma spark reactions are differentiable based on the measured chemical reaction products and reaction rates, as described in reference to blocks 322, 326 and/or 328 of FIG. 3B.

At block 604, the concentration of hydrocarbon chemical species in the collected samples of downhole fluids is determined. For example, with reference to FIG. 1, the analysis system 160 can make this determination. To determine the concentration of hydrocarbon chemical species present in the collected samples of downhole fluids, the analysis system 160 can perform operations to classify the organic chemical species present in the fluid samples through chemical analysis. The chemical analysis performed may be substantially similar to the analysis described in FIGS. 3A-3B. Organic chemical species can include hydrocarbons and other organic chemicals that may be downhole such as oxygen and hydroxyl containing compounds, nitrogen-containing compounds, phosphorus-containing compounds, etc. Chemical species that do not contain carbon, and are therefore not organic chemical species, may also be analyzed together with the hydrocarbon chemical species. The range of species analyzed can depend on the system selected for analysis (i.e. gas chromatograph, mass spectrometer, or any of the instrumentation described in reference to FIG. 1) and on the filtration system used to prepare the sample for analysis and protect the equipment. The analysis system 160 may be protected from inorganic, corrosive, caustic, or other reactive species by a pre-filter or column, such as one that removes polar substances and molecules from the analysis stream. In some embodiments, a polar substance is a chemical species in which the distribution of electrons between the covalently bonded atoms is not even. The analysis system 160 analyzes the collected fluid samples to determine the presence of organic or non-polar matter, such as hydrocarbons. The analysis system 160 can determine the presence of nonpolar gasses, such as hydrogen, carbon dioxide, etc., or such gasses may be separated from the fluid stream before analysis, such as by a phase separation membrane.

At block 606, a concentration of volatile inorganic chemical species (VICSs) in the collected sample is determined. For example, with reference to FIG. 1, the analysis system 160 can make this determination. VICSs can be inorganic chemical species that have high vapor pressure at standard temperatures and pressures. Volatile substances more readily condense or vaporize than non-volatile substances. In downhole application, VICSs can include halogens or other elements that may have become volatized. While the analysis described below is described with respect to inorganic chemical species, it may also be applied to VICS and polar chemical species. The analysis system 160 can analyze the formational and non-formational fluids in the sample at the surface or, alternately, at a location between the drill bit and the surface. The concentration of VICSs in the collected sample can be measured, and the concentration of the atoms, including trace elements, from the formation that were volatilized can be calculated from the measured concentration and based on reaction stoichiometry and reaction rates. The hydrocarbon reaction rates, such as those calculated in block 326 of FIG. 3B can be further correlated to constituents of the formation which act as catalysts or retardants of the previously determined reactions (such as those described by Equation 28).

The analysis system 160 can analyze the collected fluid samples to determine the presence of inorganic or polar matter. Common inorganic matter present in the formation that may impact chemical reactions include silica, carbon dioxide, silver, sulfur, and/or other impurities and trace elements incorporated within the formation rock or sediment. When the formation interacts with the plasma, side products can be produced in addition to the products in Equation 28. Plasma reactions can vaporize portions of the formation rock, in addition to formation fluid. For example, rocks that make up formation support structures can contain reactive and catalytic atoms in trace or substantial amounts. Such atoms, including halogen atoms, heavy metals atoms, etc., can contribute to the chemical reactions occurring as a result of the plasma generation—either as catalysts or as reactants.

Halogen-containing compounds and other volatile compounds are common side products of formation interaction: both organohalides (organochlorides, organobromides, etc.) and halogen gas (chlorine, bromine, etc.) can be produced. Such products can be inorganic (for example chlorine gas) or can be organic but polar (such as the organochloride chloroform)—neither of which are nonpolar hydrocarbons. As such, both can be filtered out before gas chromatography as they can be corrosive to chromatography columns. Other side products can form from trace metals in the formation, such as platinum, iron, manganese, etc.

The analysis system 160 can analyze the collected fluid samples to detect the presence of any side products related to the presence of non-hydrocarbon matter. One way to determine the presence of non-hydrocarbon material is through the detection of abnormal, unexpected, or odd masses in the stoichiometry of the chemical reactions, where masses of hydrocarbons are well known combinations of the atomic weights of multiples of hydrogen and carbon atoms as shown in Equation 48:

$$\text{Molecular Weight} = m*1.008 + n*12.011 \quad (48)$$

where n is the number of carbon atoms in the hydrocarbon molecule and m is the number of hydrogen atoms in the hydrocarbon molecule. Further, the relationship between m and n is defined for each type of hydrocarbon, as shown in Table 2, below. By substituting the number of hydrogen atoms (m) into Equation 48 for each type of hydrocarbon, the molecular weight as a function of the number of carbons (n) can be calculated (as shown in Table 2).

TABLE 2

Example Hydrocarbon Molecular Weights

| Type of Hydrocarbon | Number of Hydrogen Atoms | Molecular Weight (Da) |
|---|---|---|
| Alkane | m = 2n + 2 | n * 14.027 + 2.016 |
| Naphthene | m = 2n + 2 − r | n * 14.027 − r * 1.008 |
| Alkene | m = 2n | n * 14.027 |
| Alkyne | m = 2n − 2 | n * 14.027 − 2.016 |
| Polyunsaturated | m = 2n + 2 − 2d | n * 14.027 + 2.016 − 2.016 * d |

For alkanes, there are 2n+2 hydrogen atoms for n carbon atoms. For naphthenes, there are 2n+2−r hydrogen atoms for each n carbon atoms, where r represents the number of rings in each naphthene molecule. For alkenes, there are 2n hydrogen atoms for each n carbon atoms. For alkynes, there are 2n−2 hydrogen atoms for each n carbon atoms. As saturation decreases, one or more carbon-carbon double or triple bonds can be formed, and the number of hydrogens for each carbon atom can decrease. Each additional higher order bond (i.e. each π bond) can correspond to the removal of two carbon orbital (one from each carbon atom) previously bonded to hydrogen atoms, as the two carbon atoms involved in the higher order bonds switch from $sp^a$ hybridization to $sp^2$ hybridization or from $sp^2$ hybridization to sp hybridization. Therefore, poly-unsaturated hydrocarbons have the general form $C_nH_m$ where m=2n+1−2d where d represents the number of π bonds in the molecule (d is related to but not identical with the degree of unsaturation). This gives a generalized hydrocarbon atomic weight of 14.027*n+2.016−2.016*d, which, when rounded, tends to be an even molecular weight. Molecules that do not have a molecular weight in this general form can be identified as corresponding to molecules other than hydrocarbons.

Abnormal molecular masses may be masses of odd numbers, as hydrocarbon chemical reactions typically produce molecules with molecular masses with even numbers, as explained above. A spectrometer or gas chromatography-mass spectrometer may analyze the collected samples to detect the abnormal masses—i.e. masses that do not correspond to hydrocarbons—or may analyze all constituents and selectively identify masses not corresponding to saturated or poly-unsaturated hydrocarbon molecules. Table 3 shows example atoms together with their mass number and naturally occurring isotopic concentration, plus the average atomic mass in Daltons (Da) and Pauling electronegativity in electron Volts (eV) for each element.

TABLE 3

Atomic Weight and Isotopic Concentration for Example Constituent Atoms

| Element | Abbreviation | Mass Number | In Nature | Atomic Mass (Da) | Pauling Electronegativity (eV) |
|---|---|---|---|---|---|
| Hydrogen | H | 1 | 99.98% | 1.008 | 2.20 |
| Deuterium | D or $^2$H | 2 | 0.02% | | |
| Carbon | C | 12 | 98.93% | 12.011 | 2.55 |
| 13-Carbon | $^{13}$C | 13 | 1.07% | | |
| 16-Oxygen | O | 16 | 99.76% | 15.999 | 3.44 |
| 17-Oxygen | $^{17}$O | 17 | 0.04% | | |
| 18-Oxygen | $^{18}$O | 18 | 0.20% | | |
| Fluorine | F | 19 | ~100% | 18.998 | 3.98 |
| 35-Chlorine | $^{35}$Cl | 35 | 76% | 35.45 | 3.16 |
| 37-Chlorine | $^{37}$Cl | 37 | 24% | | |
| 79-Bromine | $^{79}$Br | 79 | 51% | 79.904 | 2.96 |
| 81-Bromine | $^{81}$Br | 81 | 49% | | |
| Iodine | I | 127 | ~100% | 126.90 | 2.66 |
| Manganese | $^{55}$Mn | 55 | ~100% | 54.938 | 1.55 |
| Platinum | $^{195}$Pt | 195 | 33.83% | 195.08 | 2.28 |

The analysis system 160 can determine one or more concentrations for chemical reaction product species based on mass spectrometry results. The presence of polar molecules, organohalides, metal complexes, etc., in the mass spectrograph can be correlated directly to the presence of oxygen, halogen, and metallic atoms in the formation and formation fluid, where such atoms act as reactants during the chemical reaction produced by the plasma. Several example reactions are shown below in Equations 49-52:

$$H_2C=CH_2 + HCl \rightarrow CH_3CH_2Cl \quad (49)$$

$$4HCl + O_2 \rightarrow 2Cl_2 + 2H_2O \quad (50)$$

$$FeAsS + 3O_2 \rightarrow AsO_3 + SO_2 + Fe_xO_y \quad (51)$$

$$Fe(CO)_5 + 2C_5H_6 \rightarrow Fe(C_5H_6)_2 + 5CO + H_2 \quad (52)$$

Equations 49-52 are representative of possible reactions that can occur between the chemical constituents of the formation and are mediated by the plasma. Individual atoms and molecules, including inorganic species such as chlorine gas, iron oxide, etc. can also be produced. Non-hydrocarbon side products can be formed directly from hydrocarbon and formation interactions, or from the interaction of reaction products (such as those shown in Equation 28) with the formation, or reaction products (e.g. carbon dioxide, oxygen, hydrogen) generated in one plasma event acting on the formation in a subsequent plasma event. Individual atoms, such as metals like platinum may also be found in their native states (i.e. Pt) or in oxides (such as $MnO_2$). The concentration of non-hydrocarbon constituents in the drilling fluid can range from significant percentages (water up to 10%, for example) to trace amounts (such as manganese which is found in soils in ranges of 7-9000 parts per million (ppm) and may enter drilling fluid in orders of magnitude smaller quantities).

Elements can be further determined from mass spectrometry based on their isotopic concentrations. Mass spectrometry measures a mass-to-charge ratio, where isotopes of a single element appear as neighboring peaks with heights or intensities proportional to their relative abundance. These peaks may be small satellite peaks, as for carbon where $^{13}$C is approximately 1.1% of all naturally occurring carbon, or these peaks may be of the same order of magnitude, as for bromine, where approximately 51% of naturally occurring bromine is $^{79}$Br and 49% is $^{81}$Br. The distinctive relationship between isotopes of each element can contribute to a determination of the atomic makeup of the molecules detected by mass spectrometry. The effect of isotope can be cumulative—i.e. each atom in a molecule can be an isotope, which can lead to a smearing of mass peaks for one molecule. For example, for hexane (molecular formula $C_6H_{12}$), the $^{12}$C and $^1$H peak at 86 Da is 93.49% (i.e. $0.9893^6*0.9998^{14}$) of the total detected hexane, while the peak at 87 Da is 6.33% (i.e. $6*0.0107*0.9893^5*0.9998^{14}+14*0.0002*0.9893^6*0.9998^{13}$) of the total detected hexane, when carbon and hydrogen isotopes are assumed to occur at their natural abundance. These two percentages do not sum to unity, because the small percentage of hexane molecules that contain two or more isotopes also contribute to the whole. The relationship between carbon isotopes gives rise to the general Equation 53:

$$n = \frac{100}{1.1} \frac{Y}{X} \quad (53)$$

where n is the number of carbon atoms, X is the amplitude of the ion peak at a molecular weight to charge M, and Y is the amplitude of the ion peak at a molecular weight to charge M+1. The relationships between peaks can, therefore, provide information about the atoms that make up the molecule to which the peak corresponds.

FIG. 7 depicts an example mass spectrometry graph, according to one or more embodiments. FIG. 7 depicts a mass spectrometry graph 700. The graph 700 represents an example output of quadrupole analog mass spectrometry. The graph 700 has an x-axis 701 of mass to charge ratio (mass/charge) in units of kilogram (kg)/Coulomb (C). The graph 700 has a y-axis 702 representing intensity. A line 703 represents the mass spectrum of a sample. The line 703 may have peaks 704-712. Each peak 704-712 represents an ion having a specific mass to charge ratio. The area under the peak indicates the concentration of the ion. Peaks 704, 710, 711, and 712 are single peaks most likely representing a single ion. Peaks 705, 706, and 707 and peaks 708 and 709 are clustered. Clusters of peaks may represent spectral fingerprints or satellite peaks. The cluster of peaks 705, 706, and 707 most likely represent a spectral fingerprint of water. The cluster of peaks 708 and 709 most likely represent a satellite peak of silicon.

Returning to FIG. 6 at block 608, the determined VICSs are equated to possible formation types based on mineral composition of the formation. For example, with reference to FIG. 1, the computer 162 can perform this equating of VICSs to possible formation types. Different formation types can be composed of rocks of various minerals. Minerals can be determined based on the combination of VICSs determined in the inorganic analysis. For example, some combinations of aluminum oxides and other chemical constituents may indicate the presence of chlorites, which may be indicative of igneous or metamorphic rock, while other combinations of aluminum oxides and different chemical constituents may be indicative of illite, which may be indicative of a sedimentary rock formation.

To illustrate, table 4 is an example of a table for classifying formation type based on volatile inorganic chemical species, according to one or more embodiments. Table 4 lists common minerals often found in rock formations and the some of the VICSs that may be indicative of the mineral's presence in the formation. Table 4 is provided for example purposes only, as tables used for classifying formation type may contain hundreds of possible minerals and combinations of VICSs. A sample of common minerals found in oil and gas producing formations are provided in table 4. From table 4, it can be seen that many minerals are composed of similar VICSs, but each mineral has a unique combination of VICSs. For example, silicon dioxide ($SiO_2$) is present in chlorite, albite, illite, kaolinite, and quartz. If the silicon dioxide is one of the determined VICSs, the computer 162 would select only those elements as possible minerals. If aluminum oxide ($Al_2O_3$) was also a determined VICS, the computer could eliminate quartz as a possible mineral type as quartz contains no aluminum oxide. This process can continue until all VICSs in the formation are detected or until one or more mineral types are determined.

Based on the detected VICSs, the computer 162 can determine possible minerals which correlate to formation types. For example, barite occurs is sedimentary formations such as limestone rock while dolomite occurs in sedimentary carbonate formations. The computer 162 may select possible types, eliminate possible types, or perform a combination of both. For selecting possible formation types, the computer 162 can compare the determined VICSs to the known chemical constituents of different formation types and select the formation types which contain the determined VICSs. When eliminating possible formation types, the computer 162 cannot consider any possible formation type that does not include the determined VICSs, thereby leaving behind only formation types which contain the determined VICSs as possible formation types.

to loss of energy or current to ground, reduces the energy available for chemical reactions, independent of the fluid characteristics. The reduction in energy for plasma-based chemistry shifts the possible chemical reactions because less energy is available to produce the molecular kinetic energy necessary to react transition states (i.e. activation energy $E_a$) or the energy necessary to produce products (i.e. enthalpy of formation). This can be identified in the resultant products. The shift can be exhibited in two forms: the formational compounds may catalyze the reaction, or the aqueous or organic liquid phase reactions may shift due to the introduction of reactants from the formation. These shifts are incorporated into the generalized chemical equation for plasma reactions to represent the downhole environment more accurately.

At block 612, the power loss to the formation is determined. For example, with reference to FIG. 1, the analysis system 160 can make this determination. Similar methods and equations to those described in block 306 of FIG. 3A may be used to determine the power loss to the formation. Determining the power loss may also be experimentally determined. Experimentally determining the power loss may include calculating a power loss based on equations, such as those described in FIG. 3A, or it may include monitoring the power downhole for changes.

At block 614, the power loss is equated to the possible formation types, as determined in block 608. For example, with reference to FIG. 1, the computer 162 can make this equaling of power loss to possible formation types. Conductivity is a measure of how easily electric current can flow through a given material. Conductivity represents a power loss within a material. The conductivities of different rock types are known values. Conductivities of a specific rock type may span many orders of magnitude depending on porosity, permeability, connectivity, temperature, degree of fluid saturation, etc. of the formation. For example, granite-

TABLE 4

Formation Classification based on VICSs Composition of Minerals in Rock

| Mineral | Volatile Inorganic Chemical Species | | | | | | |
|---|---|---|---|---|---|---|---|
| Rutile | $TiO_2$ | $TiO_2$ | | | | | |
| Fluorapatite | $Ca_5(PO_4)_3(F)$ | $P_2O_5$ | CaO | | | | |
| Barite | $BaSO_4$ | BaO | $SO_3$ | | | | |
| Pyrite | $FeS_2$ | $SO_3$ | | | | | |
| Chlorite | $Mg_3Fe_3Si_2Al_2 \cdot O_{10}(OH)_8$ | $Fe_2O_3$ | MgO | $Al_2O_3$ | $SiO_2$ | $(Mg, Fe)_3(Si, Al)_4O_{10}$ $(OH)_2 \cdot (Mg, Fe)_2(OH)_6$ | $Mg_{1.5}Fe_{1.5}Si_2Al_2O_{10} \cdot$ $(OH)_2Mg_{1.5}Fe_{1.5} \cdot (OH)_6$ |
| Dolomite | $Ca_{0.5}Mg_{0.5}CO_3$ | MgO | CaO | | | | |
| Calcite | $CaCO_3$ | CaO | | | | | |
| Halite | NaCl | Cl | $Na_2O$ | | | | |
| Albite (Naplagioclase) | $NaAlSi_3O_8$ | $Na_2O$ | $Al_2O_3$ | $SiO_2$ | | | |
| Illite | $KAl_4(Si_7AlO_{20}) \cdot (OH)_4$ | $K_2O$ | $Al_2O_3$ | $SiO_2$ | — | $K_{1.5-1.0}Al_4 \cdot (Si_{6.5-7.0}Al_{1.0-1.5}O_{20})$ $(OH)_4$ | |
| Kaolinite | $Al_2Si_2O_5(OH)_4$ | $Al_2O_3$ | $SiO_2$ | | | | |
| Quartz | $SiO_2$ | $SiO_2$ | | | | | |

At block 610, the generalized chemical equation for plasma reactions, such as Equation 28, is adjusted for changes due to the formation type. For example, with reference to FIG. 1, the computer 162 can make this adjustment. During plasma reactions with fluid, energy is absorbed by the formation. The conductivity of the formation itself can be independent of the formation fluid in the pore spaces (the conductivity of the formation together with the formational fluid is dependent upon the formational fluid conductivity and the permeability or interconnectedness of the fluid-filled pores). Loss of energy to the formation, similar bearing rocks are highly conductive while carbonate rocks and unconsolidated sediments are very resistive. By comparing the possible formation types, determined at block 608, to the power loss to the formation, the computer 162 can further limit possible rock and formation types. The computer 162 can compare the power loss values to the ranges of conductivities for each of the determined possible formation types. Power loss values falling within the known ranges for each rock and formation type indicate a possible match, and thus a viable rock and formation option. These options are selected, or maintained, as possible formation types. Power loss values outside a range of conductivity values for one of the determined possible formation types indicate the rock and formation type are not a match, and thus, the rock and formation type are not a viable option for the drilled formation. These rock and formation types can be removed from further analysis.

At block 616, the possible formation types are constrained based on solid composition analysis. For example, with reference to FIG. 1, the computer 162 can perform this constraining. The computer 162 may perform solid composition analysis to analyze physical samples collected from the downhole environment. Solid composition analysis may include operations for monitoring cuttings as described in block 310 of FIG. 3B. Solid composition analysis may also include analysis using techniques related to inductively coupled plasma mass spectroscopy (ICP-MS), x-ray powder diffraction (XRD), and/or x-ray fluorescence (XRF). For example, with reference to FIG. 1, the instrumentation 161 may perform this measurement and the computer 162 may perform the analysis. Solid composition analysis can provide another means of narrowing down the possible formation types. The solid composition analysis can provide at least some of the rock types contained in the formation. Based on the solid composition analysis, the computer 162 can eliminate any remaining formation types that do not contain the rocks identified in the solid composition analysis. There may be one or more rock and/or formation types remaining as possible formation types. This is possible because drilling may occur through many formation layers, and individual formation layers may contain various rock types.

At block 618, the formation type is determined. For example, with reference to FIG. 1, the computer 162 can make this determination based on operations at block 614 (and possibly operations at block 616). The determined formation type can be one or multiple types.

The flowcharts are provided to aid in understanding the illustrations and are not to be used to limit scope of the claims. The flowcharts depict example operations that can vary within the scope of the claims. Additional operations may be performed; fewer operations may be performed; the operations may be performed in parallel; and the operations may be performed in a different order. It will be understood that each block of the flowchart illustrations and/or block diagrams, and combinations of blocks in the flowchart illustrations and/or block diagrams, can be implemented by program code. The program code may be provided to a processor of a general-purpose computer, special purpose computer, or other programmable machine or apparatus.

As will be appreciated, aspects of the disclosure may be embodied as a system, method or program code/instructions stored in one or more machine-readable media. Accordingly, aspects may take the form of hardware, software (including firmware, resident software, micro-code, etc.), or a combination of software and hardware aspects that may all generally be referred to herein as a "circuit," "module" or "system." The functionality presented as individual modules/units in the example illustrations can be organized differently in accordance with any one of platform (operating system and/or hardware), application ecosystem, interfaces, programmer preferences, programming language, administrator preferences, etc.

Any combination of one or more machine readable medium(s) may be utilized. The machine-readable medium may be a machine-readable signal medium or a machine-readable storage medium. A machine readable storage medium may be, for example, but not limited to, a system, apparatus, or device, that employs any one of or combination of electronic, magnetic, optical, electromagnetic, infrared, or semiconductor technology to store program code. More specific examples (a non-exhaustive list) of the machine readable storage medium would include the following: a portable computer diskette, a hard disk, a random access memory (RAM), a read-only memory (ROM), an erasable programmable read-only memory (EPROM or Flash memory), a portable compact disc read-only memory (CD-ROM), an optical storage device, a magnetic storage device, or any suitable combination of the foregoing. In the context of this document, a machine-readable storage medium may be any tangible medium that can contain or store a program for use by or in connection with an instruction execution system, apparatus, or device. A machine-readable storage medium is not a machine-readable signal medium.

A machine-readable signal medium may include a propagated data signal with machine readable program code embodied therein, for example, in baseband or as part of a carrier wave. Such a propagated signal may take any of a variety of forms, including, but not limited to, electromagnetic, optical, or any suitable combination thereof. A machine readable signal medium may be any machine readable medium that is not a machine readable storage medium and that can communicate, propagate, or transport a program for use by or in connection with an instruction execution system, apparatus, or device.

Program code embodied on a machine-readable medium may be transmitted using any appropriate medium, including but not limited to wireless, wireline, optical fiber cable, RF, etc., or any suitable combination of the foregoing.

The program code/instructions may also be stored in a machine readable medium that can direct a machine to function in a particular manner, such that the instructions stored in the machine readable medium produce an article of manufacture including instructions which implement the function/act specified in the flowchart and/or block diagram block or blocks.

Example Computer

FIG. 8 depicts an example computer, according to one or more embodiments. The computer includes a processor 801 (possibly including multiple processors, multiple cores, multiple nodes, and/or implementing multi-threading, etc.). The computer includes a memory 807. The memory 807 may be system memory or any one or more of the above already described possible realizations of machine-readable media. The computer also includes a bus 803 and a network interface 805. The computer also includes an organic analyzer 811, an inorganic analyzer 813, and an arc and spark analyzer 815. Any one of the previously described functionalities may be partially (or entirely) implemented in hardware and/or on the processor 801. For example, the functionality may be implemented with an application specific integrated circuit, in logic implemented in the processor 801, in a co-processor on a peripheral device or card, etc. Further, realizations may include fewer or additional components not illustrated in FIG. 8 (e.g., video cards, audio cards, additional network interfaces, peripheral devices, etc.). The processor 801 and the network interface 805 are coupled to the bus 803. Although illustrated as being coupled to the bus 803, the memory 807 may be coupled to the processor 801.

While the aspects of the disclosure are described with reference to various implementations and exploitations, it will be understood that these aspects are illustrative and that the scope of the claims is not limited to them. In general, techniques for determining rock type based on plasma chemistry as described herein may be implemented with facilities consistent with any hardware system or hardware systems. Many variations, modifications, additions, and improvements are possible.

Plural instances may be provided for components, operations or structures described herein as a single instance. Finally, boundaries between various components, operations and data stores are somewhat arbitrary, and particular operations are illustrated in the context of specific illustrative configurations. Other allocations of functionality are envisioned and may fall within the scope of the disclosure. In general, structures and functionality presented as separate components in the example configurations may be implemented as a combined structure or component. Similarly, structures and functionality presented as a single component may be implemented as separate components. These and other variations, modifications, additions, and improvements may fall within the scope of the disclosure.

Use of the phrase "at least one of" preceding a list with the conjunction "and" should not be treated as an exclusive list and should not be construed as a list of categories with one item from each category, unless specifically stated otherwise. A clause that recites "at least one of A, B, and C" can be infringed with only one of the listed items, multiple of the listed items, and one or more of the items in the list and another item not listed.

Example Embodiments

Example embodiments include the following:

Embodiment 1: A method comprising: determining chemical species released into a drilling fluid after a rock of a subsurface formation has interacted with a plasma discharge produced via one or more electrodes of a drill bit of a pulse power drill string disposed in a borehole for drilling the borehole in the subsurface formation; correlating the chemical species to an attribute of the subsurface formation that interacted with the plasma discharge; and classifying a type of the rock of the subsurface formation that interacted with the plasma discharge based on the correlating.

Embodiment 2: The method of embodiment 1, wherein the attribute of the subsurface formation comprises a conductivity.

Embodiment 3: The method of embodiment 2, wherein the correlating comprises comparing a power loss to the formation after the rock of the subsurface formation has interacted with the produced plasma discharge to the conductivity.

Embodiment 4: The method of embodiments 1, 2, or 3, wherein determining the chemical species released into a drilling fluid after a rock of a subsurface formation has interacted with a plasma discharge comprises: determining concentrations of inorganic chemical species released into the drilling fluid; and determining possible types of rock of the subsurface formation based on the determined concentrations of inorganic chemical species.

Embodiment 5: The method of embodiments 1, 2, 3, or 4, wherein the interaction between the rock and the plasma discharge releases volatile inorganic chemical species related to the rock type into the drilling fluid.

Embodiment 6: The method of embodiments 1, 2, 3, 4, or 5, further comprising: determining organic chemical species released into the drilling fluid.

Embodiment 7: The method of embodiments 1, 2, 3, 4, 5, or 6, further comprising classifying a type of the rock of the subsurface formation that interacted with the plasma discharge based on an analysis of solid material from the drilled subsurface formation.

Embodiment 8: A non-transitory, computer-readable medium having instructions stored thereon that are executable by a computing device to perform operations comprising: determining chemical species released into a drilling fluid after a rock of a subsurface formation has interacted with a plasma discharge produced via one or more electrodes of a drill bit of a pulse power drill string disposed in a borehole for drilling the borehole in the subsurface formation; correlating the chemical species to an attribute of the subsurface formation that interacted with the plasma discharge; and classifying a type of the rock of the subsurface formation that interacted with the plasma discharge based on the correlating.

Embodiment 9: The non-transitory, computer-readable medium of embodiment 8, wherein the attribute of the subsurface formation comprises a conductivity.

Embodiment 10: The non-transitory, computer-readable medium of embodiment 9, wherein correlating the chemical species to an attribute of the subsurface formation that interacted with the plasma discharge comprises comparing a power loss to the formation after the rock of the subsurface formation has interacted with the produced plasma discharge to the conductivity.

Embodiment 11: The non-transitory, computer-readable medium of embodiment 8, 9, or 10, wherein determining the chemical species released into a drilling fluid after a rock of a subsurface formation has interacted with a plasma discharge comprises: determining inorganic chemical species released into the drilling fluid; and determining possible types of rock of the subsurface formation based on the determined inorganic chemical species.

Embodiment 12: The non-transitory, computer-readable medium of embodiment 8, 9, 10, or 11, wherein the interaction between the rock and the plasma discharge releases volatile inorganic chemical species related to the rock type into the drilling fluid.

Embodiment 13: The non-transitory, computer-readable medium of embodiment 8, 9, 10, 11, or 12 wherein the operations further comprise: determining organic chemical species released into the drilling fluid.

Embodiment 14: The non-transitory, computer-readable medium of embodiment 8, 9, 10, 11, 12, or 13, wherein the operations further comprise classifying a type of the rock of the subsurface formation that interacted with the plasma discharge based on an analysis of solid material from the drilled subsurface formation.

Embodiment 15: A system comprising: a pulse power drill string configured to be positioned in a borehole formed in a subsurface formation, wherein the pulse power drill string comprises a drill bit with one or more electrodes to periodically emit an electrical discharge to drill the borehole; a sample extractor configured to collect a sample of drilling fluid that circulated down the borehole after the drilling fluid has interacted with the electrical discharge; a processor; and a computer-readable medium having instructions stored thereon that are executable by the processor to cause the system to, determine chemical species released into the drilling fluid after a rock of the subsurface formation has interacted with the electrical discharge, correlate the chemical species to an attribute of the subsurface formation that interacted with the electrical discharge, and classify a type of the rock of the subsurface formation that interacted with the electrical discharge based on the correlating.

Embodiment 16: The system of embodiment 15, wherein the attribute of the subsurface formation comprises a conductivity.

Embodiment 17: The system of embodiment 16, wherein the instructions executable by the processor to cause the system to correlate comprise instructions executable by the processor to cause the system to compare a power loss to the formation after the rock of the subsurface formation has interacted with the produced plasma discharge to the conductivity.

Embodiment 18: The system of embodiment 15, 16, or 17, wherein the instructions executable by the processor to cause the system to determine the chemical species released into a drilling fluid after a rock of a subsurface formation has interacted with the electrical discharge comprise instructions executable by the processor to cause the system to: determine inorganic chemical species released into the drilling fluid; and determine possible types of rock of the subsurface formation based on the determined inorganic chemical species.

Embodiment 19: The system of embodiment 15, 16, 17, or 18, wherein the instructions further comprise instructions executable by the processor to cause the system to: determine organic chemical species released into the drilling fluid.

Embodiment 20: The system of embodiment 15, 16, 17, 18, or 19, wherein the instructions further comprise instructions executable by the processor to cause the system to: classify a type of the rock of the subsurface formation that interacted with the plasma discharge based on an analysis of solid material from the drilled subsurface formation.

As used herein, the term "or" is inclusive unless otherwise explicitly noted. Thus, the phrase "at least one of A, B, or C" is satisfied by any element from the set {A, B, C} or any combination thereof, including multiples of any element.

The invention claimed is:

1. A method comprising:
   determining the presence of one or more chemical species released into a drilling fluid as a result of a rock of a subsurface formation having interacted with a plasma discharge produced via one or more electrodes of a drill bit of a pulse power drill string disposed in a borehole for drilling the borehole in the subsurface formation;
   correlating the presence of the one or more chemical species released into the drilling fluid after the rock of the subsurface formation has interacted with the plasma discharge to an attribute of the subsurface formation; and
   classifying a type of the rock of the subsurface formation that interacted with the plasma discharge based on the correlating.

2. The method of claim 1, wherein the attribute of the subsurface formation comprises a conductivity.

3. The method of claim 2, wherein the correlating comprises comparing a power loss to the formation after the rock of the subsurface formation has interacted with the produced plasma discharge to the conductivity.

4. The method of claim 1, wherein determining the presence of one or more chemical species released into a drilling fluid as the result of the rock of the subsurface formation having interacted with the plasma discharge comprises:
   determining concentrations of one or more inorganic chemical species released into the drilling fluid; and
   determining possible types of rock of the subsurface formation based on the determined concentrations of the one or more inorganic chemical species.

5. The method of claim 1, wherein the interaction between the rock and the plasma discharge releases one or more volatile inorganic chemical species related to the rock type into the drilling fluid.

6. The method of claim 1, further comprising:
   determining the presence of one or more organic chemical species released into the drilling fluid.

7. The method of claim 1, further comprising classifying a type of the rock of the subsurface formation that interacted with the plasma discharge based on an analysis of solid material from the drilled subsurface formation.

8. A non-transitory, computer-readable medium having instructions stored thereon that are executable by a computing device to perform operations comprising:
   determining the presence of one or more chemical species released into a drilling fluid as a result of a rock of a subsurface formation having interacted with a plasma discharge produced via one or more electrodes of a drill bit of a pulse power drill string disposed in a borehole for drilling the borehole in the subsurface formation;
   correlating the presence of the one or more chemical species released into the drilling fluid after the rock of the subsurface formation has interacted with the plasma discharge to an attribute of the subsurface formation; and
   classifying a type of the rock of the subsurface formation that interacted with the plasma discharge based on the correlating.

9. The non-transitory, computer-readable medium of claim 8, wherein the attribute of the subsurface formation comprises a conductivity.

10. The non-transitory, computer-readable medium of claim 9, wherein correlating the presence of the one or more chemical species to an attribute of the subsurface formation that interacted with the plasma discharge comprises comparing a power loss to the formation after the rock of the subsurface formation has interacted with the produced plasma discharge to the conductivity.

11. The non-transitory, computer-readable medium of claim 8, wherein determining the presence of the one or more chemical species released into a drilling fluid as the result of the rock of a subsurface formation having interacted with the plasma discharge comprises:
   determining the presence of one or more inorganic chemical species released into the drilling fluid; and
   determining possible types of rock of the subsurface formation based on the determined presence of the one or more inorganic chemical species.

12. The non-transitory, computer-readable medium of claim 8, wherein the interaction between the rock and the plasma discharge releases one or more volatile inorganic chemical species related to the rock type into the drilling fluid.

13. The non-transitory, computer-readable medium of claim 8, wherein the operations further comprise:
   determining the presence of one or more organic chemical species released into the drilling fluid.

14. The non-transitory, computer-readable medium of claim 8, wherein the operations further comprise classifying a type of the rock of the subsurface formation that interacted with the plasma discharge based on an analysis of solid material from the drilled subsurface formation.

15. A system comprising:
   a pulse power drill string configured to be positioned in a borehole formed in a subsurface formation, wherein the pulse power drill string comprises a drill bit with one or more electrodes to periodically emit an electrical discharge to drill the borehole;

a sample extractor configured to collect a sample of drilling fluid that circulated down the borehole after the drilling fluid has interacted with the electrical discharge;

a processor; and a computer-readable medium having instructions stored thereon that are executable by the processor to cause the system to, determine the presence of one or more chemical species released into the drilling fluid as a result of a rock of the subsurface formation having interacted with the electrical discharge, correlate the one or more chemical species released into the drilling fluid after the rock of the subsurface formation has interacted with the electrical discharge to an attribute of the subsurface formation, and classify a type of the rock of the subsurface formation that interacted with the electrical discharge based on the correlating.

16. The system of claim 15, wherein the attribute of the subsurface formation comprises a conductivity.

17. The system of claim 16, wherein the instructions executable by the processor to cause the system to correlate comprise instructions executable by the processor to cause the system to compare a power loss to the formation after the rock of the subsurface formation has interacted with the produced plasma discharge to the conductivity.

18. The system of claim 15, wherein the instructions executable by the processor to cause the system to determine the presence of the one or more chemical species released into the drilling fluid after the rock of the subsurface formation has interacted with the electrical discharge comprise instructions executable by the processor to cause the system to:

determine the presence of one or more inorganic chemical species released into the drilling fluid; and determine possible types of rock of the subsurface formation based on the determined presence of the one or more inorganic chemical species.

19. The system of claim 15, wherein the instructions further comprise instructions executable by the processor to cause the system to:

determine the presence of one or more organic chemical species released into the drilling fluid.

20. The system of claim 15, wherein the instructions further comprise instructions executable by the processor to cause the system to:

classify a type of the rock of the subsurface formation that interacted with the plasma discharge based on an analysis of solid material from the drilled subsurface formation.

* * * * *